United States Patent
Heil et al.

(10) Patent No.: US 8,748,010 B2
(45) Date of Patent: Jun. 10, 2014

(54) MATERIALS FOR ORGANIC ELECTROLUMINESCENT DEVICES

(75) Inventors: Holger Heil, Darmstadt (DE); Arne Buesing, Frankfurt am Main (DE); Philipp Stoessel, Frankfurt am Main (DE); Horst Vestweber, Gilserberg (DE); Amir Hossain Parham, Frankfurt (DE)

(73) Assignee: Merck Patent GmbH (DE)

( * ) Notice: Subject to any disclaimer, the term of this patent is extended or adjusted under 35 U.S.C. 154(b) by 1371 days.

(21) Appl. No.: 12/064,751

(22) PCT Filed: Jul. 26, 2006

(86) PCT No.: PCT/EP2006/007386
§ 371 (c)(1),
(2), (4) Date: Feb. 25, 2008

(87) PCT Pub. No.: WO2007/022845
PCT Pub. Date: Mar. 1, 2007

(65) Prior Publication Data
US 2008/0193797 A1 Aug. 14, 2008

(30) Foreign Application Priority Data
Aug. 26, 2005 (DE) .......................... 10 2005 040 411

(51) Int. Cl.
*H01L 51/54* (2006.01)

(52) U.S. Cl.
USPC ...... 428/690; 428/917; 257/40; 257/E51.049; 313/504; 313/506; 252/301.16

(58) Field of Classification Search
None
See application file for complete search history.

(56) References Cited

U.S. PATENT DOCUMENTS

| 2001/0021478 A1* | 9/2001 | Shi et al. ...................... 430/57.1 |
| 2002/0086180 A1 | 7/2002 | Seo et al. |
| 2007/0063189 A1 | 3/2007 | Schwalm et al. |

FOREIGN PATENT DOCUMENTS

| EP | 1491568 A1 | 12/2004 | |
| JP | 2000/003790 A * | 1/2000 | ............. H05B 33/22 |
| JP | 2002-083680 A | 3/2002 | |
| JP | 2003-238516 A | 8/2003 | |
| JP | 2005-068087 A | 3/2005 | |
| JP | 2005-108441 A | 4/2005 | |
| JP | 2007-505074 A | 3/2007 | |

OTHER PUBLICATIONS

English language machine translation of JP 2000/003790 A, 2000.*
Le Berre "Autoxidation of orthoquinoid indenofluorene hydrocarbons" Ann. Chim. (Paris), 1957. vol. 2, pp. 371-425.*
Dahlmann et al., "The Diyne Reaction of 3,3'-Bis(phenylethynl)-2,2'-bithiophene Derivatives via Rhodium Compleses: A Novel Apprach to Condensed Benzo[2,1-*b*:3,4-b']dithiophenes", *Helvetica Chemica Acta*, vol. 80, pp. 111-120 (1997).
Zhang et al., "New Synthetic Approaches to Polycyclic Aromatic Hydrocarbons and Their Carcinogenic Oxidized Metabolites: Derivatives of Benzo[s]picene, Benzo[rst]pentaphene, and Dibenzo[b,def]chrysene", J. Org. Chem., V. 65, pp. 3952-3960 (2000).
Dittmer et al., "Derivatives of Thiacyclobutene (Thiete). IV. Thermal Decomposition of a Naphthothiete Sulfone. An Oxidation-Reduction Reaction and Formation of a Cyclic Sulfinate Ester (Sultine)", *The Journal of Organic Chemistry*, vol. 34, No. 5, pp. 1310-1316 (1969).
Black et al., "Modified Vilsmeier Reactions of Activated Benzofurans with Indolines: Synthesis of Benzofuran-fused Benzocarbazoles", *Tetrahedron Letters*, vol. 40, pp. 4251-4254 (1999).
Lacassagne et al., "Memoires et Communications", Academie Des Sciences,vol. 251, No. 14, pp. 1322-1324 (1960).

* cited by examiner

*Primary Examiner* — Michael H Wilson
(74) *Attorney, Agent, or Firm* — Drinker Biddle & Reath LLP

(57) ABSTRACT

The present invention relates to compounds of the formula (1) and to the use thereof in organic electroluminescent devices. The compounds of the formula (1) are used as host material or dopant in the emitting layer and/or as hole-transport material and/or as electron-transport material.

13 Claims, No Drawings

MATERIALS FOR ORGANIC ELECTROLUMINESCENT DEVICES

RELATED APPLICATIONS

This application is a national stage application (under 35 U.S.C. §371) of PCT/EP2006/007386, filed Jul. 26, 2006, which claims benefit of German application 10 2005 040 411.1, filed Aug. 26, 2005.

Organic semiconductors are being developed for a number of different applications which can be ascribed to the electronics industry in the broadest sense. The structure of organic electroluminescent devices (OLEDs) in which these organic semiconductors are employed as functional materials is described, for example, in U.S. Pat. Nos. 4,539,507, 5,151, 629, EP 0676461 and WO 98/27136. However, these devices still exhibit considerable problems which require urgent improvement:

1. The operating lifetime is still short, in particular in the case of blue emission, meaning that it has to date only been possible to achieve simple applications commercially.
2. Some of the compounds used are only sparingly soluble in common organic solvents, which makes their purification in the synthesis, but also the cleaning of the plants in the production of the organic electronic devices more difficult.
3. Some of the compounds used, which otherwise exhibit good properties in OLEDs, do not have a sufficiently high glass transition temperature.

In fluorescent OLEDs, various fused aromatic compounds, in particular anthracene or pyrene derivatives, are used in accordance with the prior art as host materials, especially for blue-emitting electroluminescent devices, for example 9,10-bis(2-naphthyl)anthracene (U.S. Pat. No. 5,935,721). WO 03/095445 and CN 1362464 describe 9,10-bis(1-naphthyl) anthracene derivatives for use in OLEDs. Further anthracene derivatives which are suitable as host materials are described in WO 01/076323, in WO 01/021729, in WO 04/013073, in WO 04/018588, in WO 03/087023 or in WO 04/018587. Host materials based on aryl-substituted pyrenes and chrysenes are described in WO 04/016575. It is necessary for high-quality applications to have improved host materials available.

The prior art which can be mentioned in the case of blue-emitting compounds is the use of certain arylvinylamines by Idemitsu (for example WO 04/013073, WO 04/016575, WO 04/018587). Very long lifetimes with dark-blue emission are quoted therewith. However, these results are highly dependent on the host material used, meaning that the quoted lifetimes cannot be compared as absolute values, but instead always only on use in an optimised system. Furthermore, these compounds are thermally unstable and cannot be evaporated without decomposition, which therefore requires high technical complexity for OLED production and thus represents a significant technical disadvantage. A further disadvantage is the emission colour of these compounds. Whereas Idemitsu quotes dark-blue emission (CIE y coordinates in the range from 0.15-0.18), it has not been possible to reproduce these colour coordinates in simple devices in accordance with the prior art. By contrast, green-blue emission is obtained here. It is not apparent how blue emission can actually be produced with these compounds. It is necessary for high-quality applications to have improved emitters available, in particular with respect to device and sublimation stability.

The matrix material used in phosphorescent OLEDs is frequently 4,4'-bis-(N-carbazolyl)biphenyl (CBP). The disadvantages are, inter alia, short life-times of the devices produced therewith and frequently high operating voltages, which result in low power efficiencies. In addition, CBP has an insufficiently high glass transition temperature. Furthermore, it has been found that CBP is unsuitable for blue-emitting electroluminescent devices, which results in poor efficiency. In addition, the structure of the devices is complex if CBP is used as matrix material since a hole-blocking layer and an electron-transport layer additionally have to be used. Improved triplet matrix materials based on keto compounds of spirobifluorene are described in WO 04/093207. For the best of the matrix materials described therein, however, toxic inorganic cyanides are required in the synthesis, meaning that the preparation of these materials is ecologically unacceptable. The glass transition temperature of other matrix materials of those described therein is still unsatisfactory.

The electron-transport compound used in organic electroluminescent devices is usually $AlQ_3$ (aluminium trishydroxyquinolinate) (U.S. Pat. No. 4,539,507). This has a number of disadvantages: it cannot be vapour-deposited without a residue, since it partially decomposes at the sublimation temperature, which represents a major problem, in particular for production plants. A further disadvantage is the strong hygroscopicity of $AlQ_3$, likewise the low electron mobility, which results in higher voltages and thus in lower power efficiency. In order to prevent short circuits in the display, it would be desired to increase the layer thickness; this is not possible with $AlQ_3$ owing to the low charge-carrier mobility and the resultant increase in voltage. Furthermore, the inherent colour of $AlQ_3$ (yellow in the solid), which can result in colour shifts, precisely in the case of blue OLEDs, due to re-absorption and weak re-emission, proves to be very unfavourable. Blue OLEDs can only be produced here with considerable losses in efficiency and colour location impairment. In spite of the said disadvantages, $AlQ_3$ to date still represents the best compromise for the multifarious requirements of an electron-transport material in OLEDs.

There thus continues to be a demand for improved materials, in particular host materials for blue-fluorescing emitters and host materials for triplet emitters, but also for emitters, hole-transport materials and electron-transport materials which result in good efficiencies and at the same time in long lifetimes in organic electronic devices, give reproducible results in the production and operation of the device and are readily accessible synthetically.

Surprisingly, it has been found that compounds which contain the novel structural units described below have significant improvements compared with the prior art. Using these materials, an increase in the efficiency and lifetime of the organic electronic device is possible compared with materials in accordance with the prior art. Furthermore, these materials are very highly suitable for use in organic electronic devices since they have a high glass transition temperature. The present invention therefore relates to these materials and to the use thereof in organic electronic devices.

The invention relates to compounds of the formula (1)

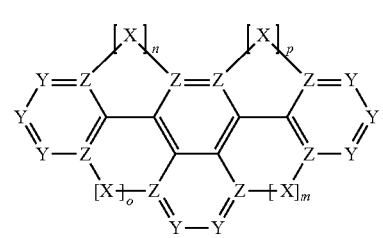

Formula (1)

where the following applies to the symbols and indices used:

Y is on each occurrence, identically or differently, $CR^1$ or N; or (Y—Y) or (Y=Y)
(i.e. two adjacent Y) stands for $NR^1$, S or O; with the proviso that each ring is a five- or six-membered ring;
Z is equal to C if a bridge X is bonded to the group Z, and is equal to Y if no bridge X is bonded to the group Z;
$R^1$ is on each occurrence, identically or differently, H, F, Cl, Br, I, $N(Ar)_2$, $C(=O)Ar$, $P(=O)(Ar)_2$, $S(=O)Ar$, $S(=O)_2Ar$, $CR^2=CR^2Ar$, CN, $NO_2$, $Si(R^2)_3$, $B(OR^2)_2$, a straight-chain alkyl, alkoxy or thioalkoxy group having 1 to 40 C atoms or a branched or cyclic alkyl, alkoxy or thioalkoxy group having 3 to 40 C atoms, which may in each case be substituted by one or more radicals $R^2$, where one or more non-adjacent $CH_2$ groups may be replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by F, Cl, Br, I, CN or $NO_2$, or an aromatic or heteroaromatic ring system having 5 to 40 aromatic ring atoms, which may in each case be substituted by one or more radicals $R^2$, or an aryloxy or heteroaryloxy group having 5 to 40 aromatic ring atoms, which may be substituted by one or more radicals $R^2$, or a combination of these systems; two or more adjacent substituents $R^1$ here may also form a mono- or polycyclic aliphatic or aromatic ring system with one another, where the formation of aromatic ring systems is only permissible on X;
Ar is on each occurrence, identically or differently, an aromatic or heteroaromatic ring system having 5-30 aromatic ring atoms, which may be substituted by one or more non-aromatic radicals $R^1$; two radicals Ar on the same nitrogen atom may also be linked to one another here by a single bond or a bridge X;
$R^2$ is on each occurrence, identically or differently, H or an aliphatic, aromatic or heteroaromatic hydrocarbon radical having 1 to 20 C atoms; two or more adjacent substituents $R^2$ here may also form a mono- or polycyclic aliphatic or aromatic ring system with one another;
X is on each occurrence, identically or differently, a divalent bridge selected from $B(R^1)$, $C(R^1)_2$, $Si(R^1)_2$, C=O, $C=NR^1$, $C=C(R^1)_2$, O, S, S=O, $SO_2$, $N(R^1)$, $P(R^1)$, $P(=O)R^1$, $P(=S)R^1$ or a combination of 2, 3 or 4 of these systems;
n, m, p, o are on each occurrence, identically or differently, 0 or 1, with the proviso that m+p=1 or 2 and n+o =1 or 2, where n=0 and m=0 and p=0 and o=0 in each case means that the corresponding bridge X is not present;
characterised in that at least one substituent $R^1$ containing at least one aryl or heteroaryl group is present.

The compound of the formula (1) preferably has a glass transition temperature $T_g$ of greater than 70° C., particularly preferably greater than 100° C., very particularly preferably greater than 130° C.

For the purposes of this invention, an aryl group contains 6 to 40 C atoms; for the purposes of this invention, a heteroaryl group contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a fused aryl or heteroaryl group in the sense of the following definition.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system will be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ethers, etc., will also be taken to mean aromatic ring systems for the purposes of this invention. Part of the aromatic or heteroaromatic ring system may also be a fused group in the sense of the following definition.

For the purposes of this invention, a fused aryl group is taken to mean a ring system having 10 to 40 aromatic ring atoms in which at least two aromatic rings are "fused" to one another, i.e. are condensed to one another, i.e. have at least one common edge and one common aromatic π-electron system. For the purposes of this invention, a fused heteroaryl group is taken to mean a ring system having 8 to 40 ring atoms in which at least two aromatic or heteroaromatic rings, at least one of which is heteroaromatic, are fused to one another. These ring systems may be substituted or unsubstituted. Examples of fused aryl or heteroaryl groups are naphthalene, quinoline, benzothiophene, anthracene, phenanthrene, phenanthroline, pyrene, perylene, chrysene, acridine, etc., while biphenyl, for example, is not a fused aryl group since there is no common edge between the two ring systems therein. Fluorene, for example, is likewise not a fused aromatic ring system since the two phenyl units therein do not form a common aromatic ring system.

For the purposes of the present invention, a $C_1$- to $C_{40}$-alkyl group, in which individual H atoms or $CH_2$ groups may also be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-40 aromatic ring atoms, which may also in each case be substituted by the above-mentioned radicals R and which may be linked to the aromatic or heteroaromatic ring via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, Preference is given to compounds of the formula (1) which contain 0, 1, 2 or 3 heteroatoms, identically or differently, in each of the two outer, non-fused aryl or heteroaryl groups and may be substituted by in each case one or two radicals $R^1$. Particular preference is given to compounds of the formula (1) in which the two outer, non-fused aryl or heteroaryl groups each, identically or differently, stand for benzene, pyridine, pyrimidine, pyrazine, pyridazine or thiophene, each of which may be substituted by one or two radicals $R^1$, in particular for benzene, which may be substituted by one or two radicals $R^1$, in particular by one radical $R^1$.

Preference is furthermore given to compounds of the formula (1) in which the central fused aryl or heteroaryl group stands, identically or differently on each occurrence, for a naphthalene group or for a fused heteroaryl group having 1 or 2 heteroatoms, each of which may be substituted by one or two radicals $R^1$. The central fused aryl or heteroaryl group particularly preferably stands for naphthalene, quinoxaline, quinoline, isoquinoline, benzopyrimidine, benzothiadiazole, benzooxadiazole, benzothiophene, benzotriazole, benzofuran or indole, very particularly preferably for naphthalene, quinoline, isoquinoline or quinoxaline, in particular naphthalene, which may in each case be substituted by one or two radicals $R^1$.

Preference is furthermore given to structures of the formula (1) in which n+o=1 and m+p=1.

Particular preference is given to structures of the formula (2), (3) or (4)

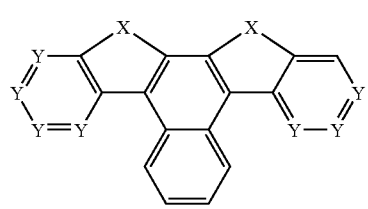

Formula (2)

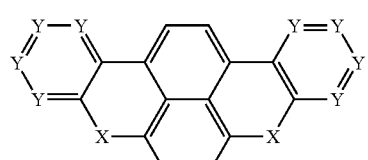

Formula (3)

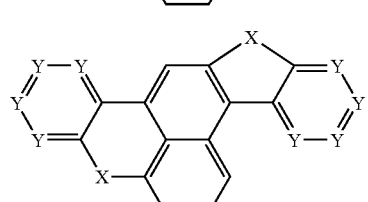

Formula (4)

where the symbols X and Y have the same meaning as described above, and the central naphthalene group may be substituted by one or more radicals $R^1$.

Very particular preference is given to structures of the formula (2a), (3a) or (4a)

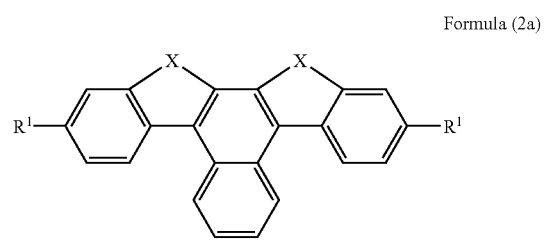

Formula (2a)

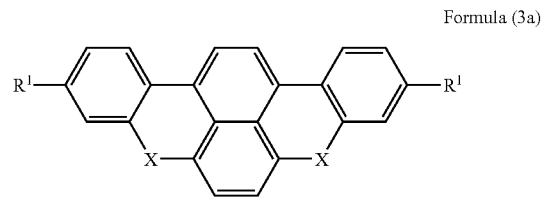

Formula (3a)

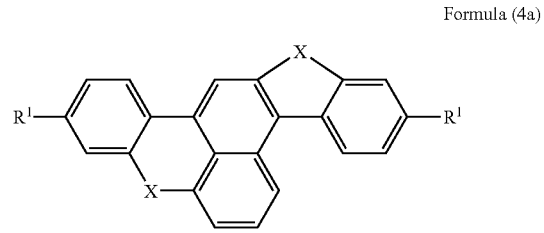

Formula (4a)

where the symbols X and $R^1$ have the same meaning as described above, and the naphthalene group may be substituted by one or more radicals $R^1$.

In the structures of the formulae (2a), (3a) and (4a), both radicals $R^1$ are particularly preferably not equal to hydrogen. The central naphthalene group is furthermore preferably unsubstituted in these structures.

Preference is furthermore given to compounds of the formulae (1), (2), (3) and (4) or (2a), (3a) and (4a) in which the symbol $R^1$ stands, identically or differently on each occurrence, for H, F, C(=O)Ar, P(=O)(Ar)$_2$, CR$^2$=CR$^2$Ar, a straight-chain alkyl group having 1 to 5 C atoms or a branched alkyl group having 3 to 5 C atoms, where one or more non-adjacent CH$_2$ groups may be replaced by —R$^2$C=CR$^2$—, —C≡C— or —O— and where one or more H atoms may be replaced by F, or an aryl group having 6 to 16 C atoms or heteroaryl group having 2 to 16 C atoms or a spirobifluorene group, which may in each case be substituted by one or more radicals $R^2$, or a combination of two or three of these systems. On incorporation into polymers, oligomers or dendrimers, linear or branched alkyl chains having up to 10 C atoms are also preferred.

Preference is furthermore given to compounds of the formulae (1), (2), (3) and (4) or (2a), (3a) and (4a) in which the symbol $R^1$ stands, identically or differently on each occurrence, for a group N(Ar)$_2$ of the formula (5) or (6)

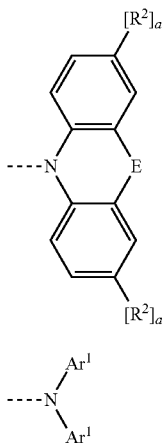

Formula (5)

Formula (6)

where R² has the meaning indicated above and furthermore:
E stands for a single bond, O, S, N(R²) or C(R²)₂;
Ar¹ is, identically or differently on each occurrence, an aryl or heteroaryl group having 5 to 20 aromatic ring atoms or a triarylamine group having 15 to 30 aromatic ring atoms, which may in each case be substituted by one or more radicals R², preferably an aryl or heteroaryl group having 6 to 14 aromatic ring atoms or a triarylamine group having 18 to 22 aromatic ring atoms, which may in each case be substituted by one or more radicals R²;
a is on each occurrence, identically or differently, 0 or 1.

Ar¹ particularly preferably stands, identically or differently, for phenyl, ortho-, meta- or para-tolyl, para-fluorophenyl, 1-naphthyl, 2-naphthyl, triphenylamine, naphthyldiphenylamine or dinaphthylphenylamine.

Preference is furthermore given to compounds of the formulae (1), (2), (3) and (4) or (2a), (3a) and (4a) in which the symbols X are on each occurrence, identically or differently, a divalent bridge selected from C(R¹)₂, C=O, C=NR¹, O, S, S=O, SO₂, N(R¹), P(R¹), P(=O)R¹, C(R¹)₂—C(R¹)₂, C(R¹)₂—C(R¹)₂—C(R¹)₂, C(R¹)₂—O and C(R¹)₂—O—C(R¹)₂. Particular preference is given to compounds of the formulae (1), (2) and (3) or (2a) and (3a) in which the symbols X are on each occurrence, identically or differently, selected from C(R¹)₂, N(R¹), P(R¹) and P(=O)(R¹), very particularly preferably C(R¹)₂ and N(R¹), in particular C(R¹)₂. It should again be explicitly pointed out here that a plurality of adjacent radicals R¹ here may also form an aromatic or aliphatic ring system with one another. If a plurality of radicals R¹ on a group C(R¹)₂ form a ring system with one another, this results in Spiro structures. The formation of Spiro structures of this type by formation of ring systems between two groups R¹ on C(R¹)₂ is a further preferred embodiment of the invention. This applies, in particular, if R¹ stands for a substituted or unsubstituted phenyl group and the two phenyl groups together with the bridge X form a ring system.

Preference is furthermore given to symmetrical and symmetrically substituted compounds, i.e. compounds of the formulae (1), (2) and (3) or (2a) and (3a) in which the two outer, non-fused aryl or heteroaryl groups are identical and in which the symbols X are identical. The substituents R¹ in the structures (2a), (3a) and (4a) are furthermore preferably selected to be identical.

Examples of compounds of the formula (1) are structures (1) to (56) depicted below.

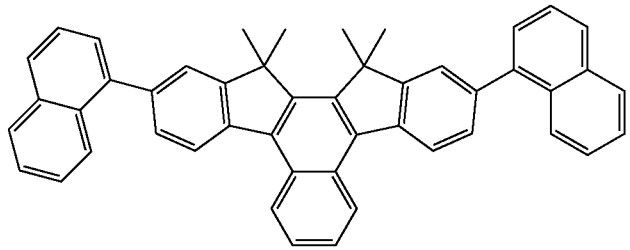

(1)

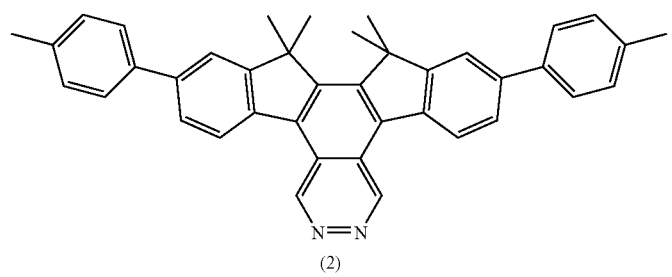

(2)

-continued
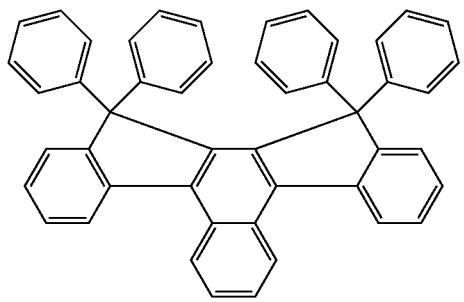
(3)
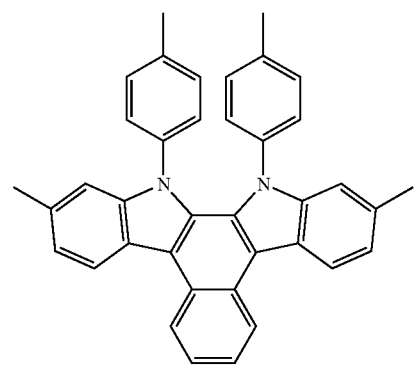
(4)
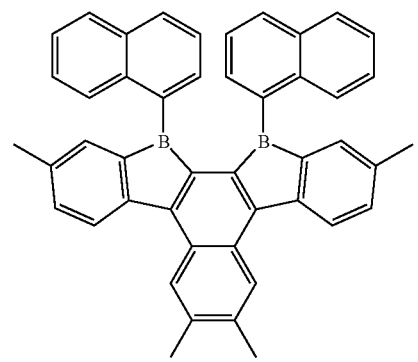
(5)
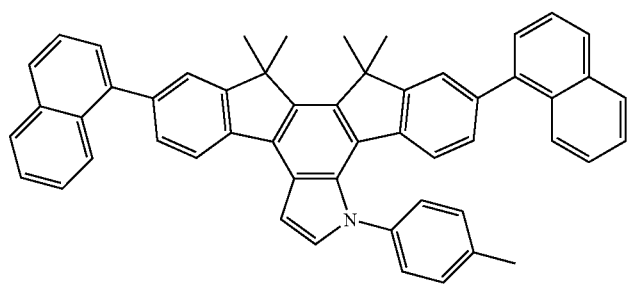
(6)

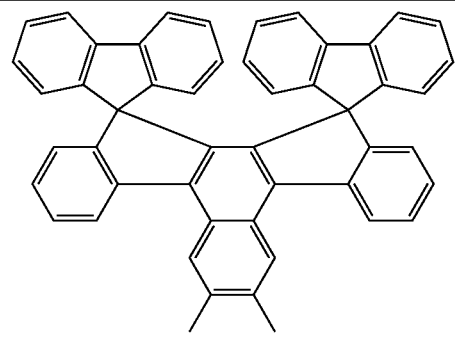
(7)
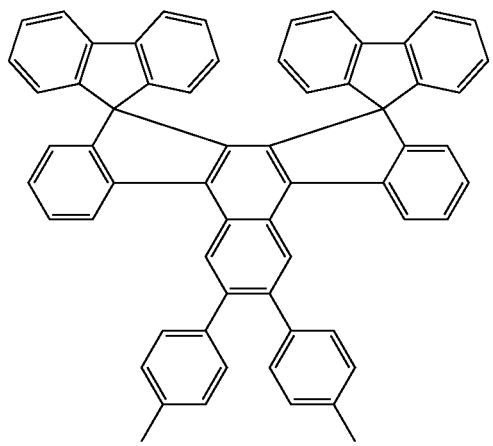
(8)
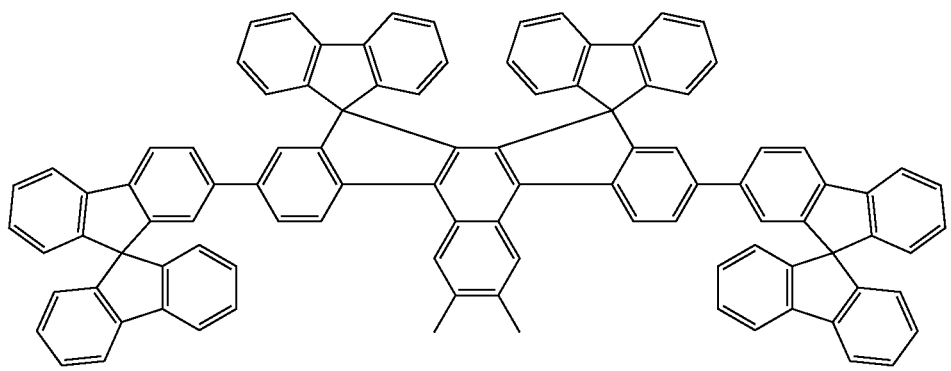
(9)
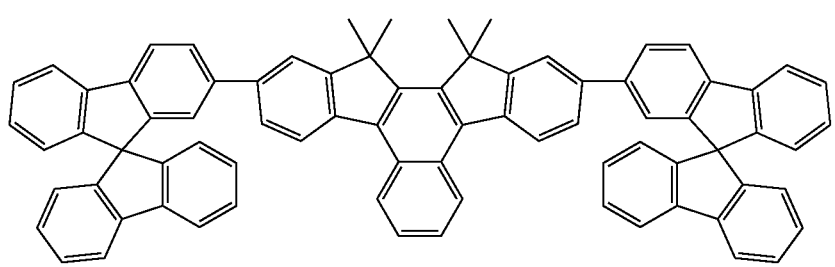
(10)

-continued
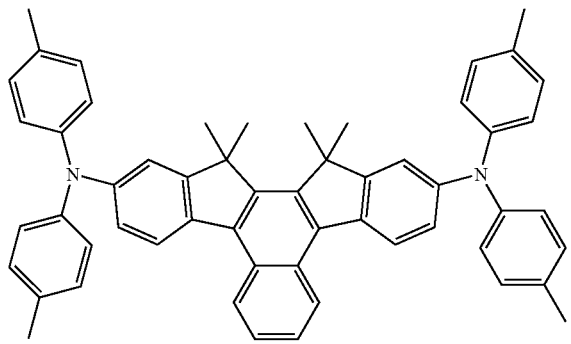
(11)
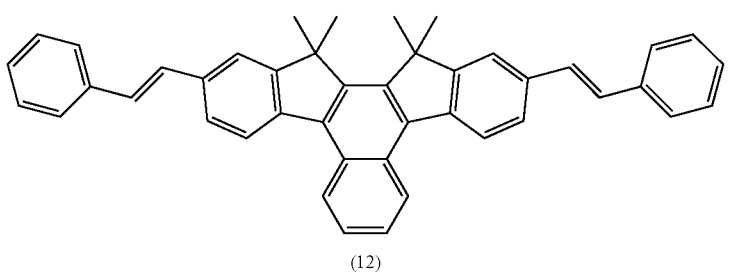 [SMILES: CC1(C)c2cc(/C=C/c3ccccc3)ccc2-c2c1c1c(c3ccccc23)-c2ccc(/C=C/c3ccccc3)cc2C1(C)C]
(12)
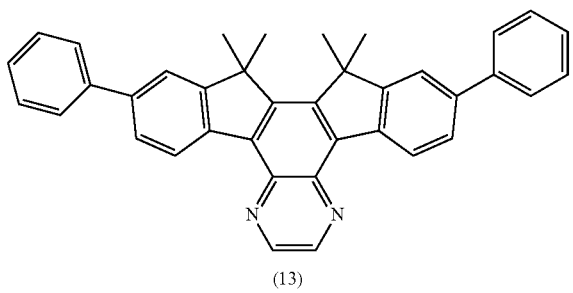 [SMILES: CC1(C)c2cc(-c3ccccc3)ccc2-c2c1c1c(c3nccnc23)-c2ccc(-c3ccccc3)cc2C1(C)C]
(13)
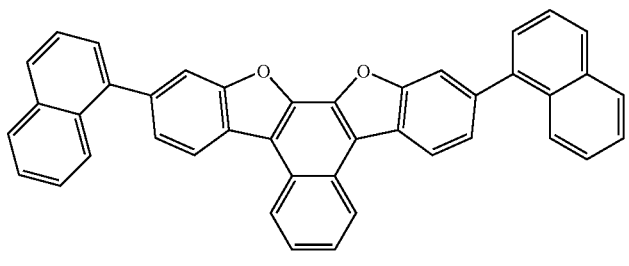
(14)
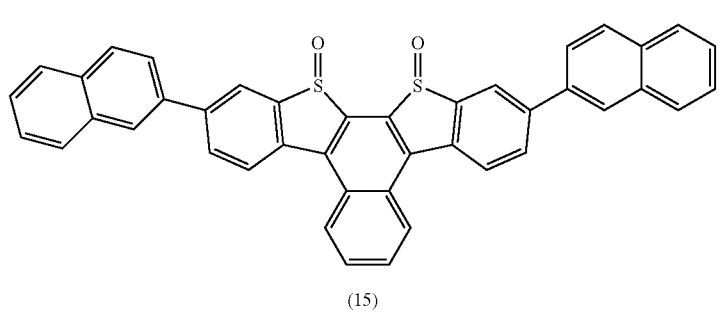 [SMILES: O=S1c2cc(-c3ccc4ccccc4c3)ccc2-c2c1c1c(c3ccccc23)-c2ccc(-c3ccc4ccccc4c3)cc2S1=O]
(15)

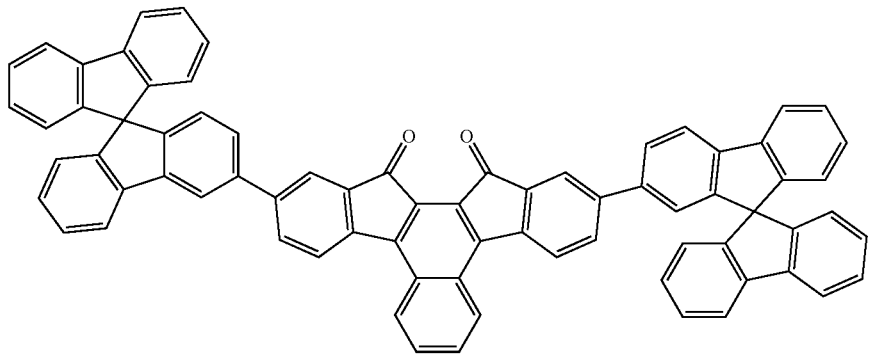
(16)
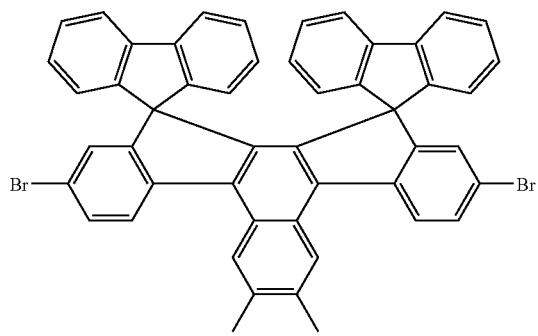
(17)
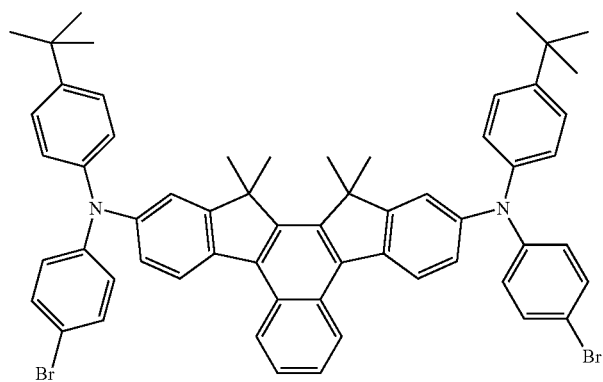
(18)
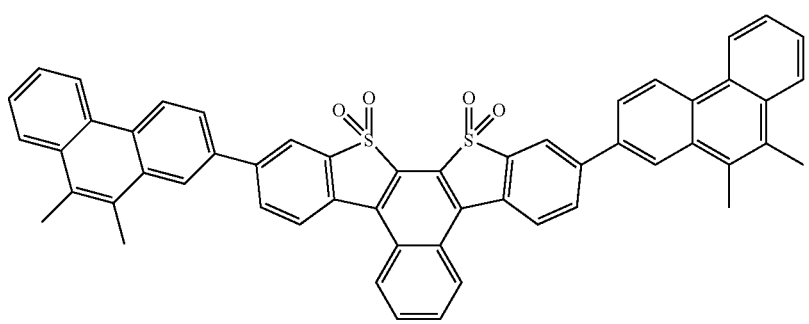
(19)

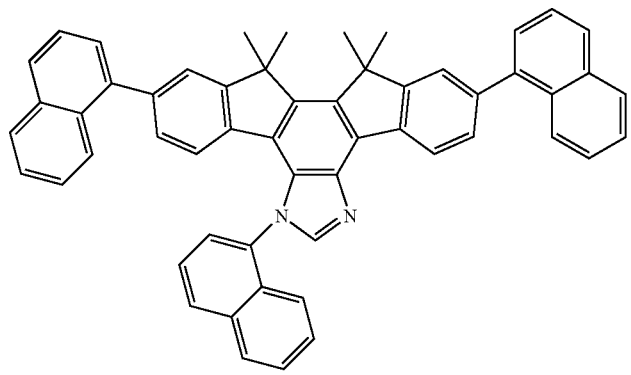
(20)
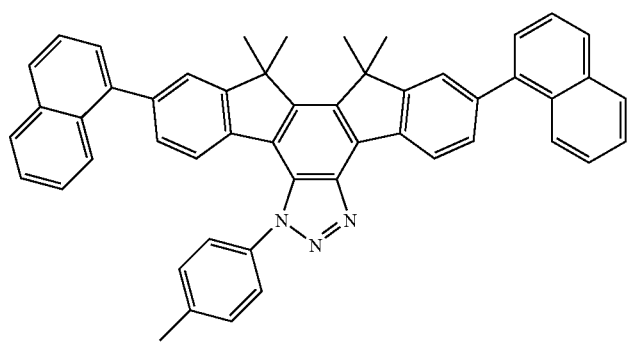
(21)
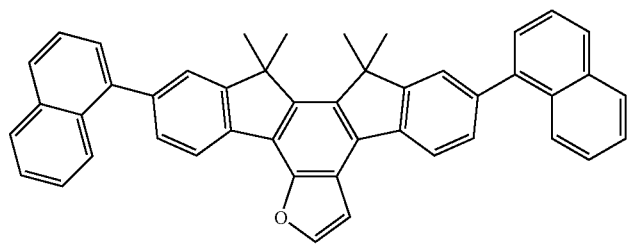
(22)
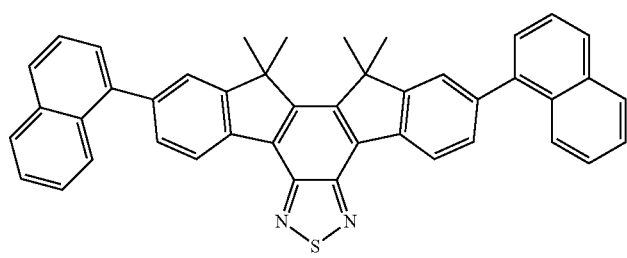
(23)

-continued
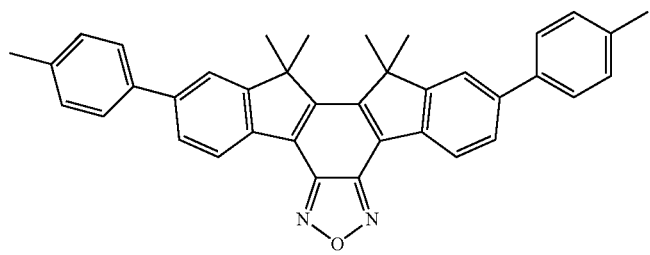
(24)
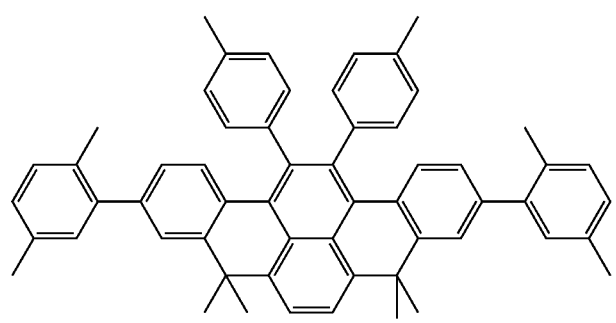
(25)
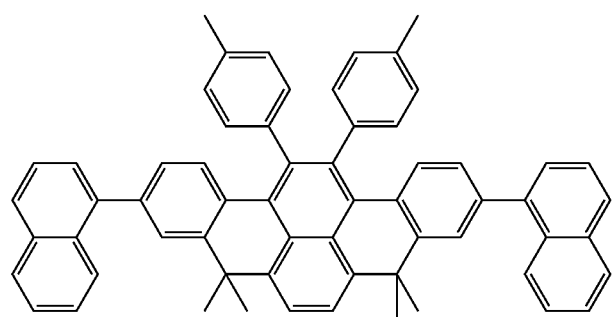
(26)
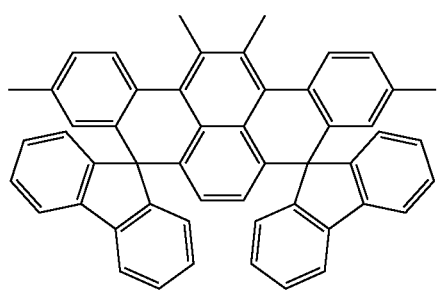
(27)
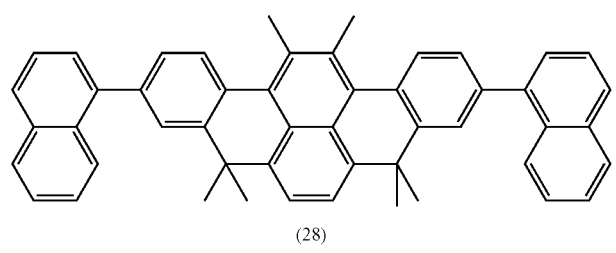 [SMILES: Cc1c(C)c2c3c(ccc4c3c1-c1ccc(-c3cccc5ccccc35)cc1C4(C)C)C(C)(C)c1cc(-c3cccc4ccccc34)ccc1-2]
(28)

-continued
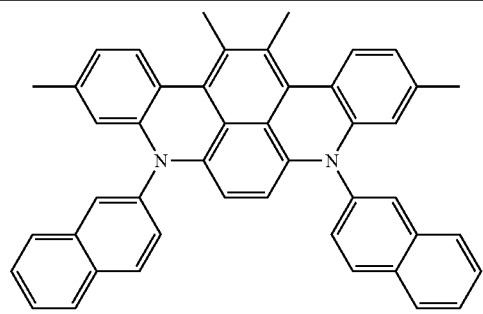
(29)
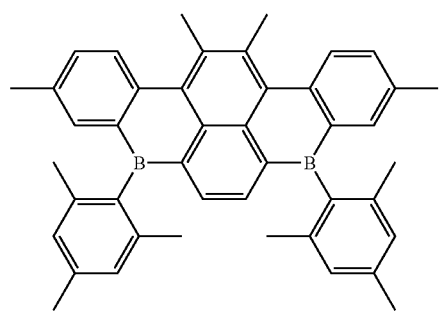
(30)
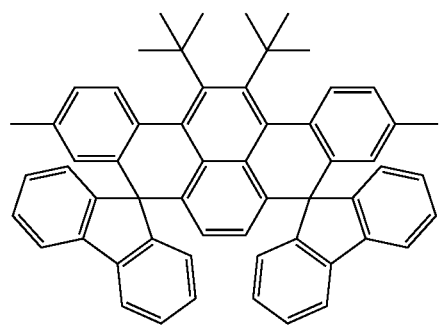
(31)
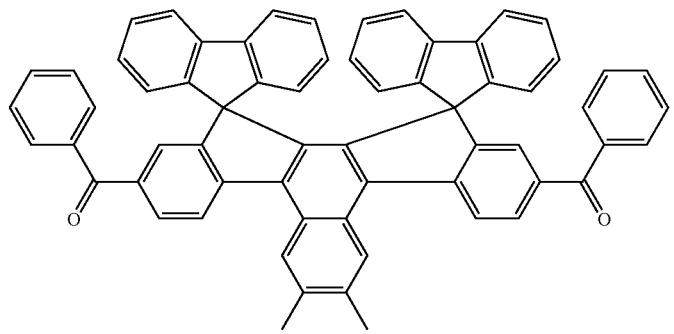
(32)

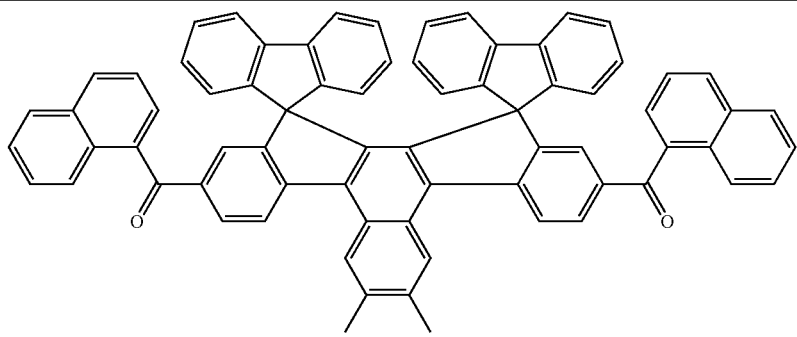
(33)
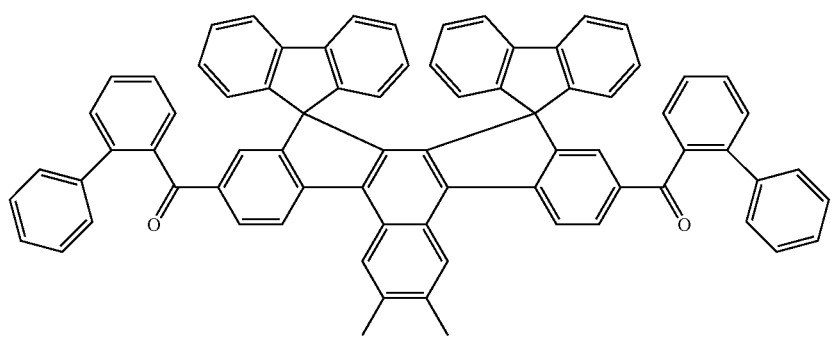
(34)
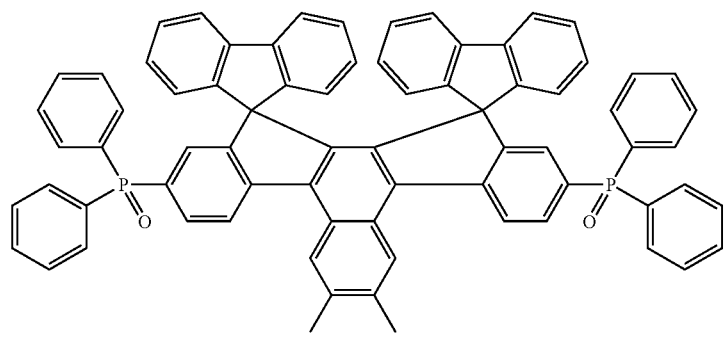
(35)
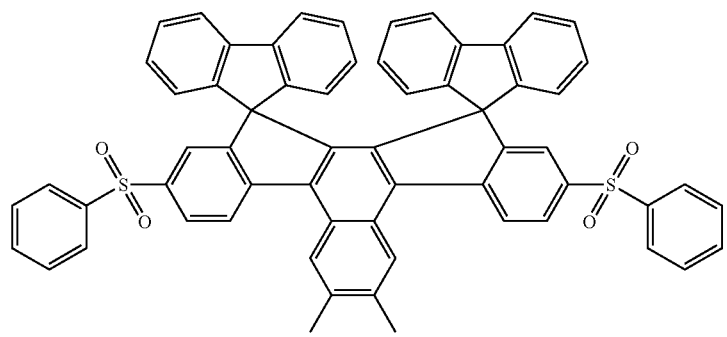
(36)

-continued
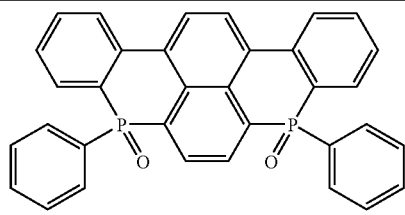
(37)
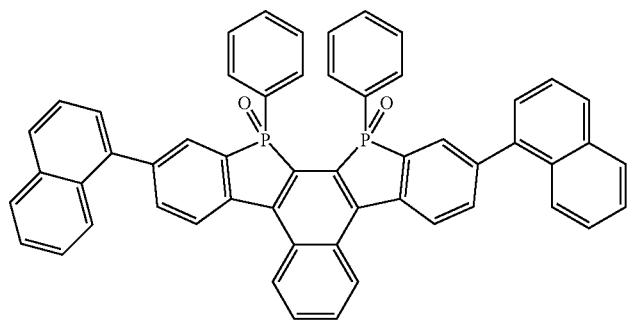
(38)
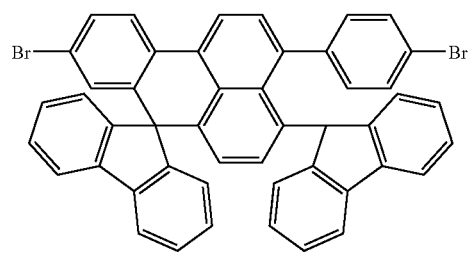
(39)
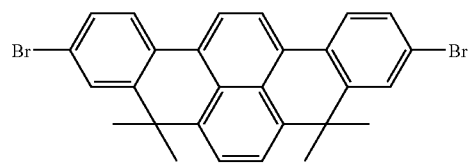
(40)
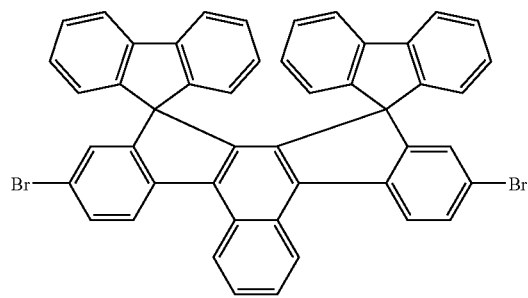
(41)

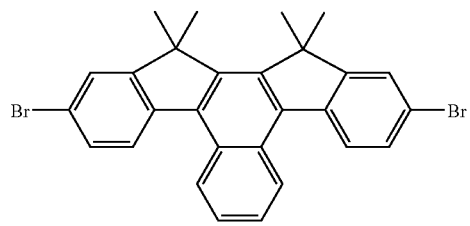
(42)
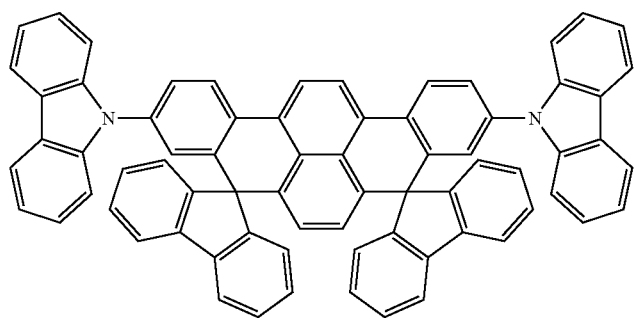
(43)
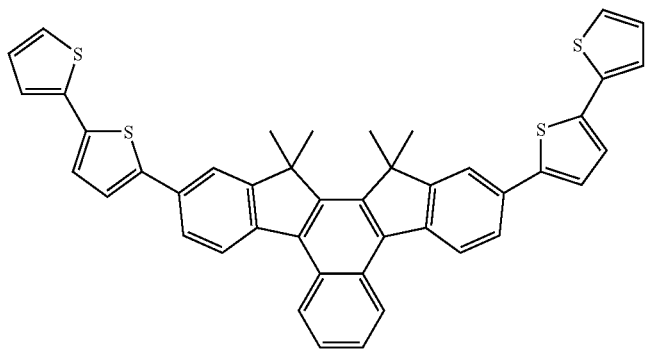
(44)
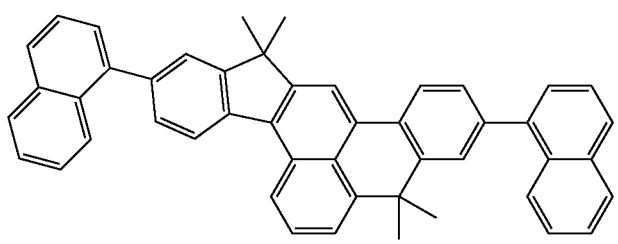
(45)

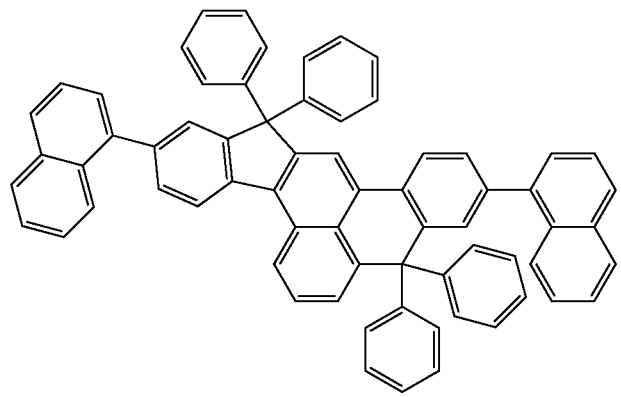
(46)
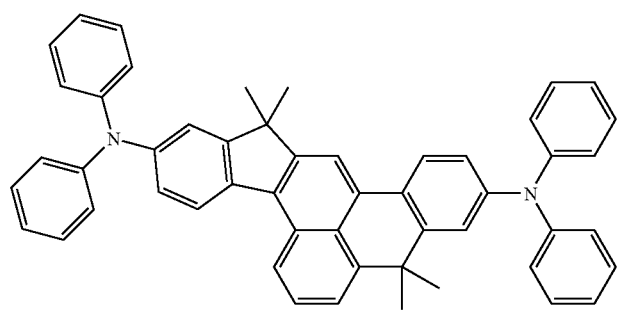
(47)
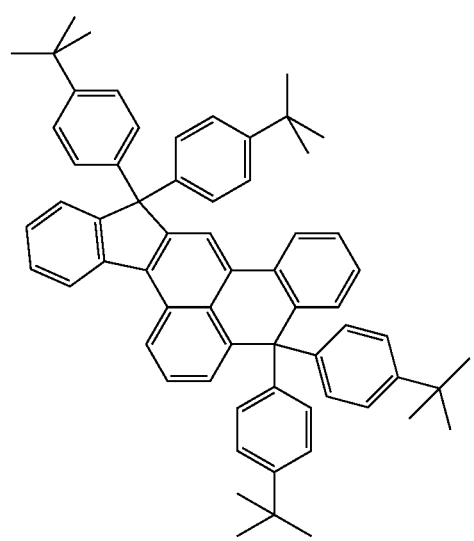
(48)

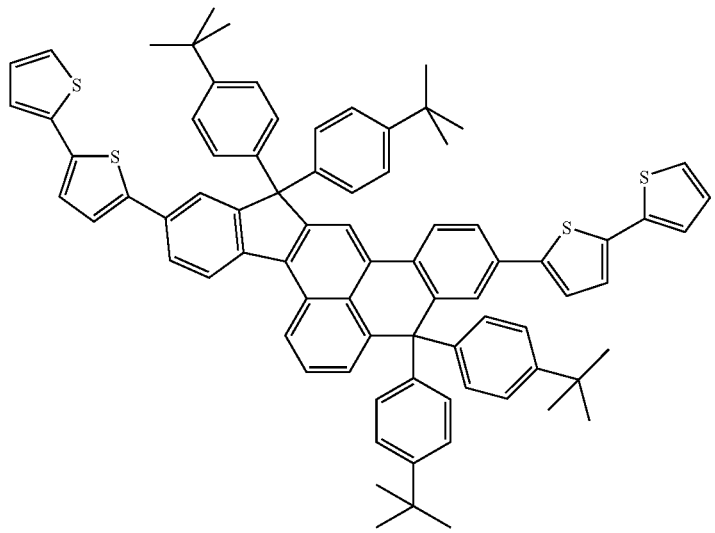
(49)
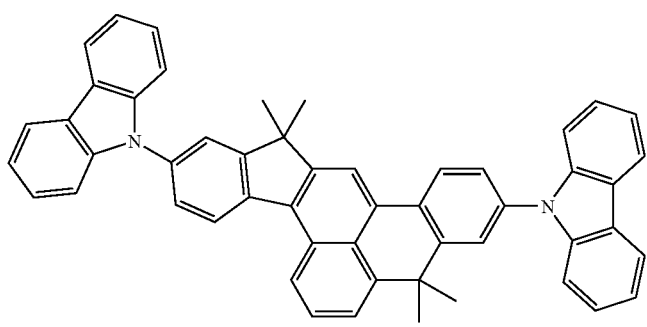
(50)
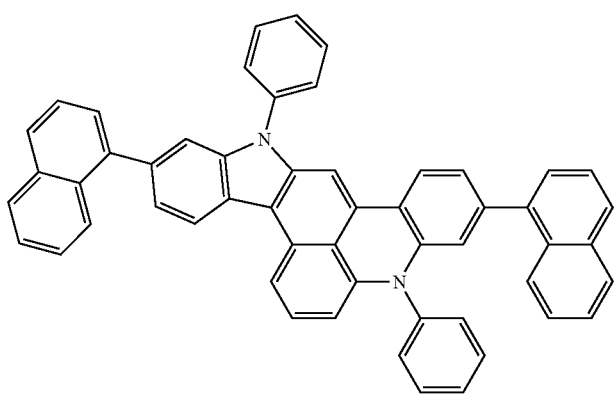
(51)

-continued
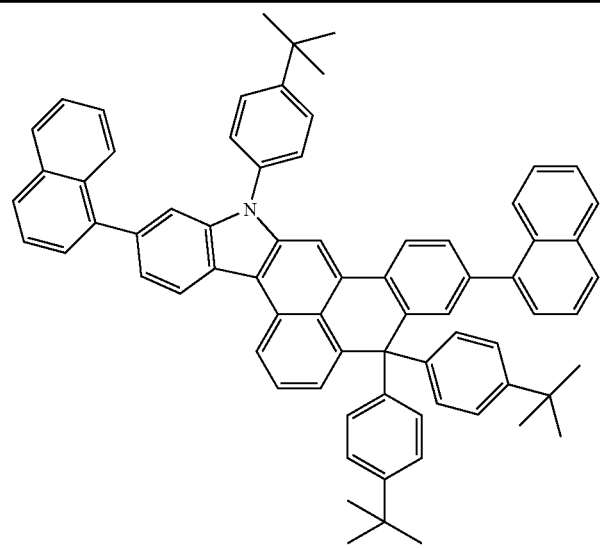
(52)
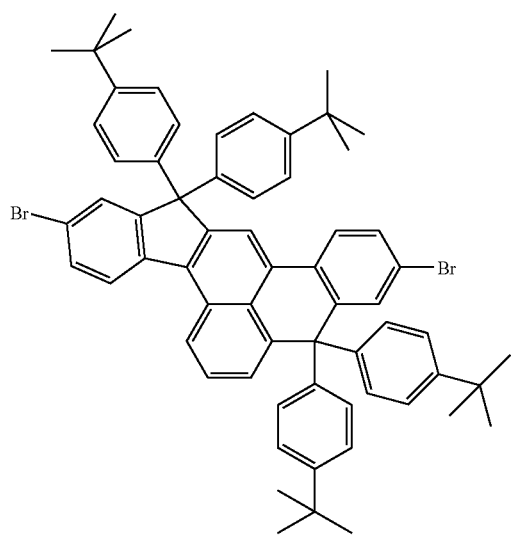
(53)
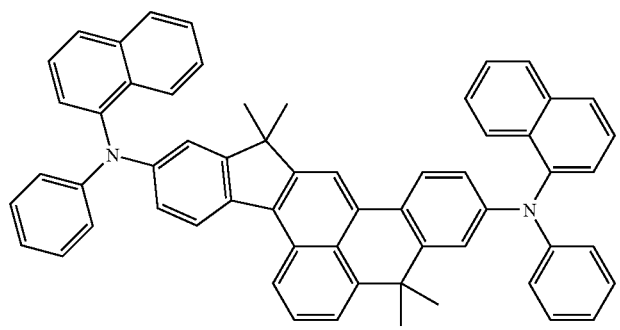
(54)

-continued

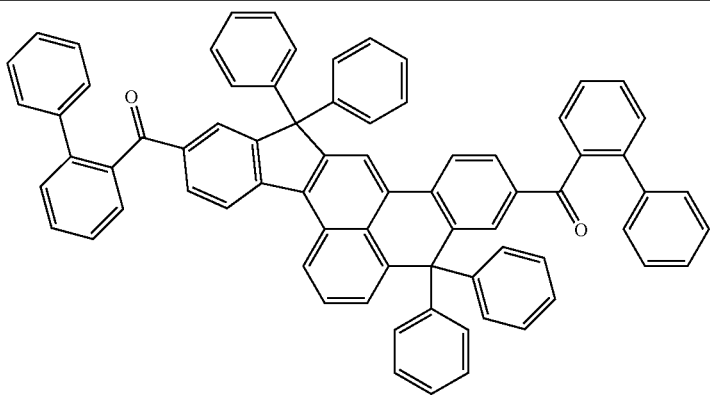

(55)

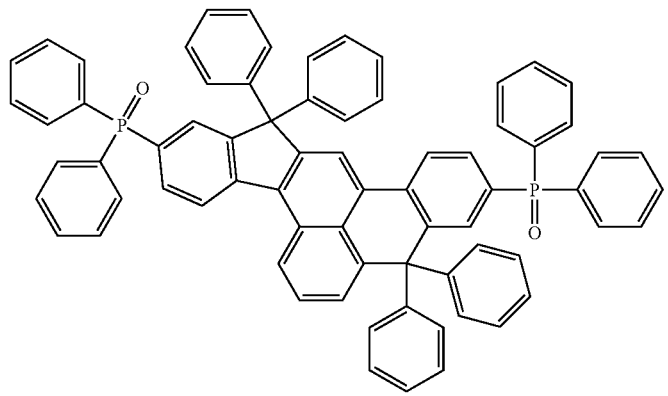

(56)

The above-described compounds according to the invention, in particular compounds which are substituted by reactive leaving groups, such as bromine, iodine, boronic acid or borate, for example compounds of structures 17, 18, 39, 40, 41, 42 and 53, may also be used as comonomers for the production of corresponding conjugated, partially conjugated or non-conjugated polymers, oligomers or also as the core of dendrimers. The polymerisation here is preferably carried out via the halogen functionality or the boronic acid functionality.

The invention thus furthermore relates to conjugated, partially conjugated and non-conjugated polymers, oligomers or dendrimers comprising one or more compounds of the formula (1), where one or more radicals $R^1$ represent bonds from the compound of the formula (1) to the polymer or dendrimer.

The same preferences as described above apply to the recurring units of the formula (1) in polymers, oligomers and dendrimers.

The recurring units of the formula (1) are preferably copolymerised with further comonomers. Suitable and preferred comonomers are selected from fluorenes (for example in accordance with EP 842208 or WO 00/22026), spirobifluorenes (for example in accordance with EP 707020, EP 894107 or EP 04028865.6), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or the as yet unpublished application DE 102005037734.3), or also a plurality of these units. These polymers usually also comprise further units, for example emitting (fluorescent or phosphorescent) units, such as, for example, vinyltriarylamines (for example in accordance with the as yet unpublished application DE 102005060473.0) or phosphorescent metal complexes (for example in accordance with WO 06/003000), and/or charge-transport units, in particular those based on triarylamines.

The compounds according to the invention can be prepared by synthetic steps known to the person skilled in the art, such as, for example, bromination, Suzuki coupling, Hartwig-Buchwald coupling, acylation, alkylation, oxidative cyclisation, etc.

Compounds having a benzo[rst]pentaphene-5,8-dione skeleton can be prepared, for example, by oxidative cyclisation of 1,4-dibenzoylnaphthalene in a eutectic aluminium chloride/sodium chloride melt (scheme 1).

Scheme 1:

Step 1:

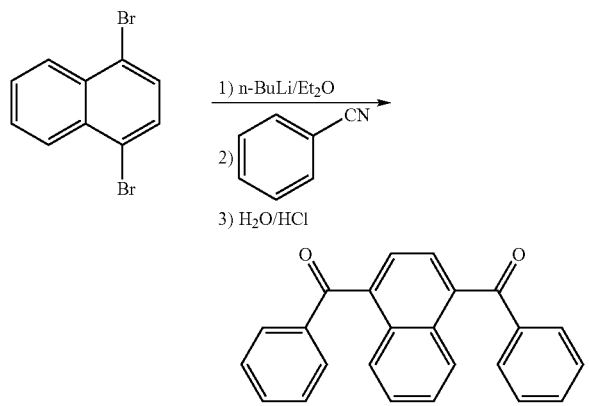

Step 2:

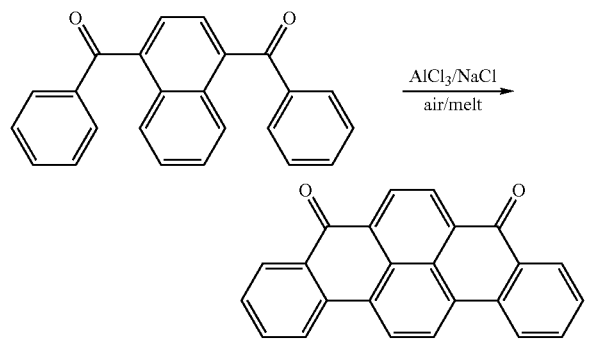

The subsequent reduction of the resultant benzo[rst]pentaphene-5,8-dione skeleton using hydrazine hydrate by the Wolf-Kishner or Huang-Minlon method, followed by methylation and final bromination, gives the synthone 3,10-dibromo-5,5,8,8-tetramethylbenzo[rst]pentaphene (scheme 2).

Scheme 2:

Step 3:

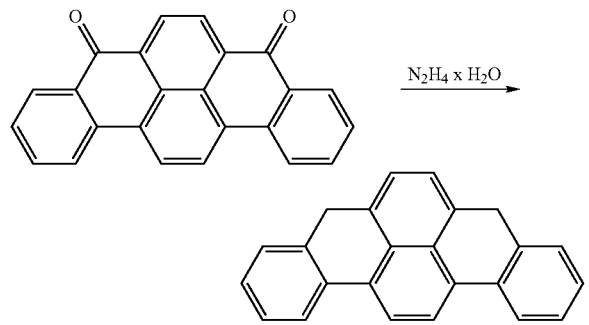

Step 4:

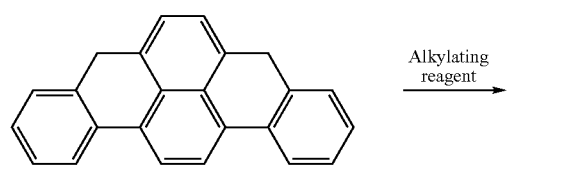

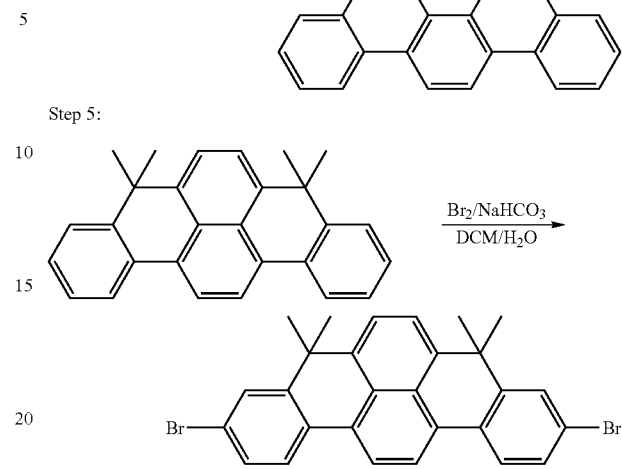

3,10-Dibromo-5,5,8,8-tetramethylbenzo[rst]pentaphene can then, for example, be converted into extended aromatic hydrocarbons by Suzuki coupling with arylboronic acids and arylboronic acid derivatives, into triarylamine derivatives by Buchwald coupling to diarylamines or into ketones via lithiation and reaction with electrophiles, such as benzonitrile, and subsequent acidic hydrolysis, or reacted with chlorodiphenylphosphines followed by oxidation to give phosphine oxides (scheme 3).

Scheme 3:

Step 6:

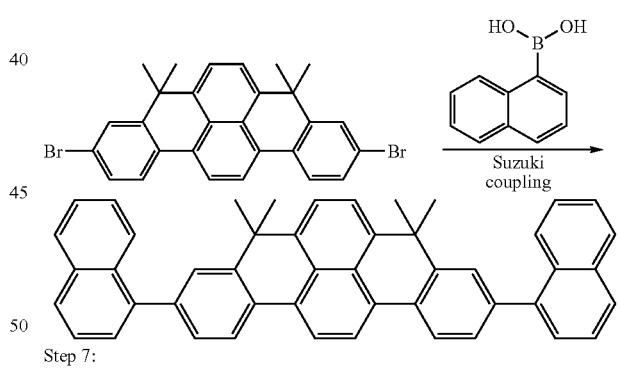

Step 7:

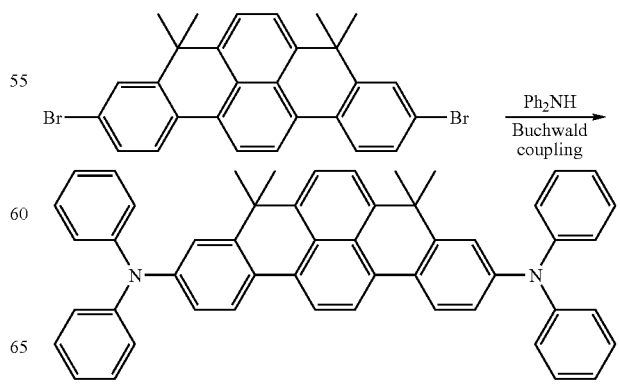

Step 8:

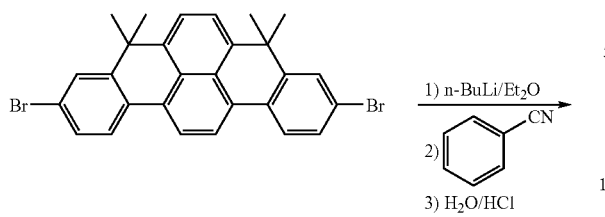

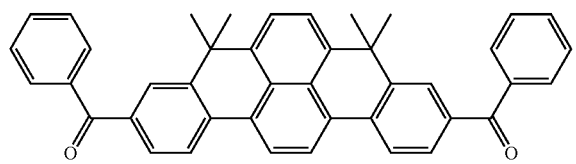

Step 9:

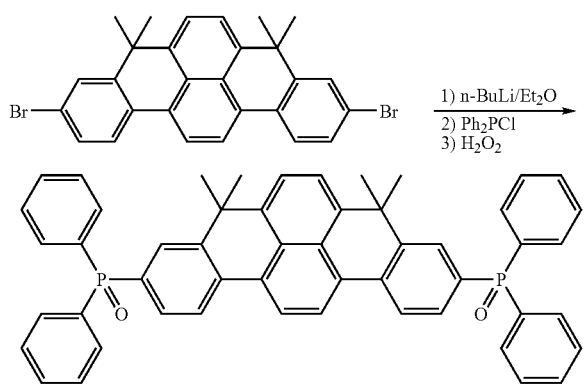

The bromination can of course also be carried out on the benzo[rst]penta-phene-5,8-dione skeleton. Subsequent reaction with biphenyl-2-magnesium bromide and acid-catalysed cyclisation of the intermediate triarylmethanol gives the corresponding spiro compound of benzo[rst]pentaphene (scheme 4), which can be further functionalised as described in scheme 3.

Scheme 4:

Step 10:

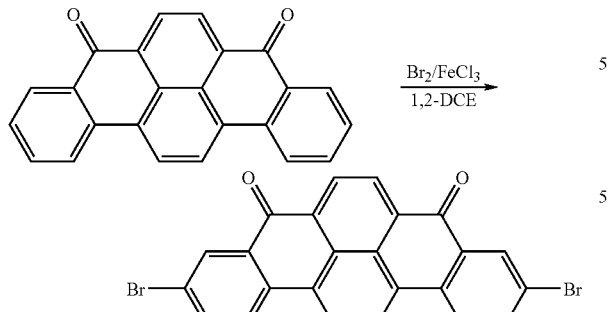

Step 11:

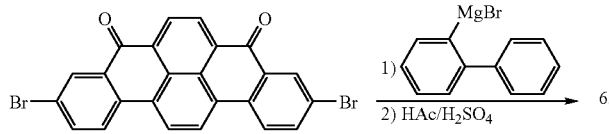

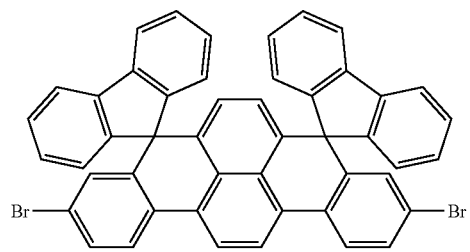

Benz[c]indeno[2,1-a]fluorene-13,14-dione can be prepared as described in *Bulletin Chem. Soc. Jpn.* 1977, 50(1), 273. The bromination is possible using elemental bromine in the presence of anhydrous iron(III) chloride (analogously to scheme 2). The 2,11-dibromobenz[c]indeno[2,1-a]fluorene-13,14-dione obtained in this way can be further functionalised analogously to schemes 2, 3 and 4.

An alternative structure of the skeletons is possible starting from 1,4-bis(2-methoxycarbonylphenyl)naphthalene, as depicted in scheme 5. This is reacted with an organometallic reagent to give the corresponding tertiary alcohol, which is cyclised with acid catalysis. The ratio of the isomers formed depends on the substituents and the precise synthetic conditions. The further functionalisation can be carried out as described above.

Scheme 5:

Step 1:

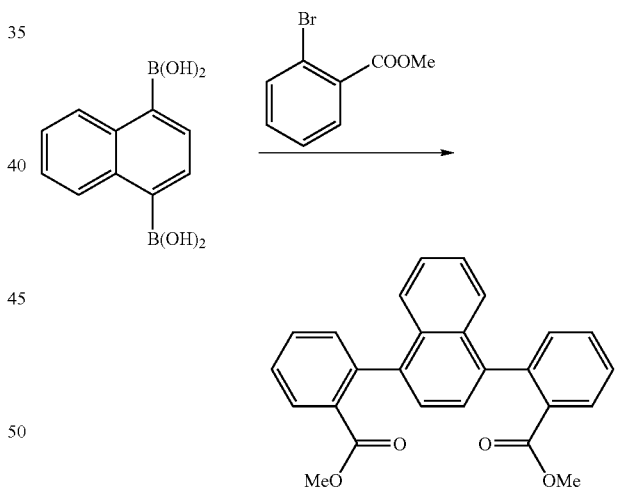

Step 2:

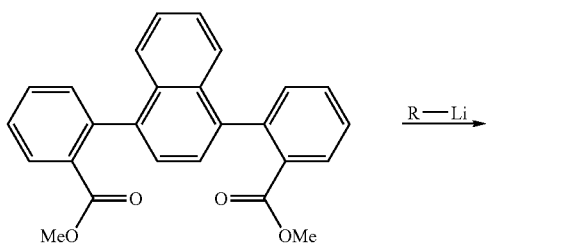

-continued

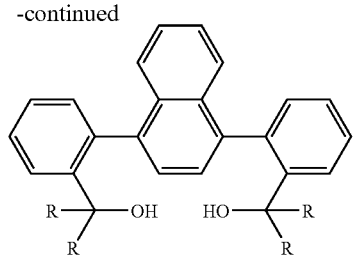

Step 3:

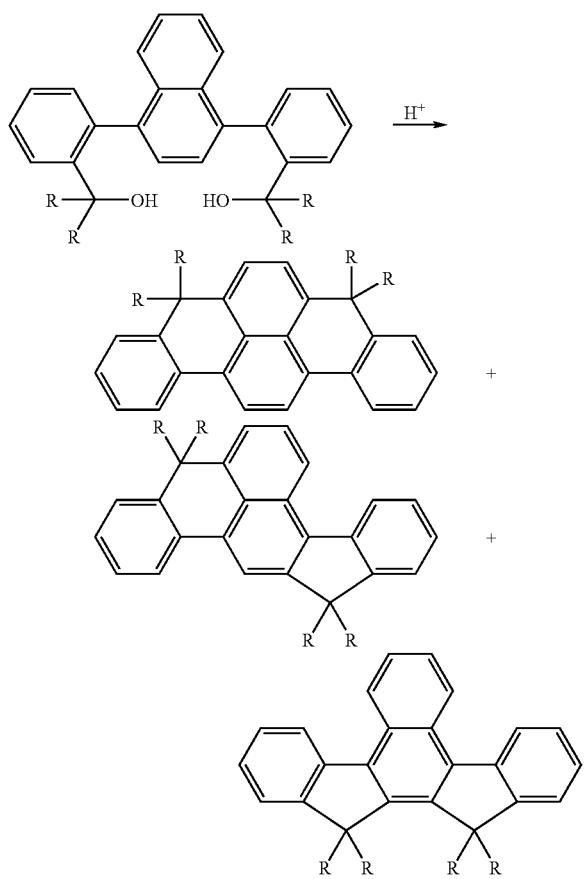

The brominated compounds can furthermore be employed, either directly or after conversion into a boronic acid derivative, as monomers for polymers, oligomers or dendrimers.

In the synthesis, depending on the synthetic conditions, both the 5-membered ring/5-membered ring derivatives and also the 6-membered ring/6-membered ring derivatives, the 5-membered ring/6-membered ring derivatives or mixtures of these compounds may be formed. These can either be separated and processed further as pure compounds or also employed as a mixture.

The compounds of the formula (1) are very highly suitable for use in organic electroluminescent devices (OLEDs, PLEDs). Depending on the substitution, the compound is employed in various functions in the OLED.

The invention therefore furthermore relates to the use of compounds of the formula (1) in organic electronic devices, in particular in organic electroluminescent devices.

The invention still further relates to organic electronic devices comprising at least one compound of the formula (1), in particular organic electroluminescent devices comprising anode, cathode and at least one emitting layer, characterised in that at least one organic layer comprises at least one compound of the formula (1).

Apart from the cathode, anode and the emitting layer, the organic electroluminescent device may also comprise further layers. These can be, for example: hole-injection layer, hole-transport layer, electron-transport layer, electron-injection layer and/or charge-generation layer (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). However, it should be pointed out that each of these layers does not necessarily have to be present.

In a further preferred embodiment of the invention, the organic electroluminescent device comprises a plurality of emitting layers, where at least one layer comprises at least one compound of the formula (1). These emission layers particularly preferably have in total a plurality of emission maxima between 380 nm and 750 nm, so that overall white emission results, i.e. various emitting compounds, which can fluoresce or phosphoresce and emit yellow, orange or red light, are used in the emitting layers. Particular preference is given to three-layer systems, where at least one of these layers comprises at least one compound of the formula (1) and where the three layers exhibit blue, green and orange or red emission (for the basic structure, see, for example, WO 05/011013). Likewise suitable for white emission are emitters which have broadband emission bands and thus exhibit white emission.

On use of the compounds of the formula (1) as host for a fluorescent dopant, preference is given to one or more substituents $R^1$ selected from simple or fused aryl or heteroaryl groups, in particular phenyl, ortho-, meta- or para-biphenyl, 1- or 2-naphthyl, anthryl, in particular phenylanthryl or 1- or 2-naphthylanthryl, 2-fluorenyl and 2-spirobifluorenyl, each of which may be substituted by one or more radicals $R^2$. This applies, in particular, to the radicals $R^1$ on the structures of the formulae (2a), (3a) and (4a).

A host material in a system comprising host and dopant is taken to mean the component which is present in higher proportion in the system. In a system comprising one host and a plurality of dopants, the host is taken to mean the component whose proportion is the highest in the mixture.

The proportion of the host material of the formula (1) in the emitting layer is between 50.0 and 99.9% by weight, preferably between 80.0 and 99.5% by weight, particularly preferably between 90.0 and 99.0% by weight. The proportion of the dopant is correspondingly between 0.1 and 50.0% by weight, preferably between 0.5 and 20.0% by weight, particularly preferably between 1.0 and 10.0% by weight.

In fluorescent devices, the dopant is preferably selected from the class of the monostyrylamines, the distyrylamines, the tristyrylamines, the tetrastyrylamines and the arylamines. A monostyrylamine is taken to mean a compound which contains one styryl group and at least one amine, which is preferably aromatic. A distyrylamine is taken to mean a compound which contains two styryl groups and at least one amine, which is preferably aromatic. A tristyrylamine is taken to mean a compound which contains three styryl groups and at least one amine, which is preferably aromatic. A tetrastyrylamine is taken to mean a compound which contains four styryl groups and at least one amine, which is preferably aromatic. For the purposes of this invention, an arylamine or an aromatic amine is taken to mean a compound which contains three aromatic or heteroaromatic ring systems bonded directly to the nitrogen, at least one of these preferably being a fused ring system having at least 14 aromatic ring atoms. The styryl groups are particularly preferably stilbenes, which may also be further substituted on the double bond or on the aromatic ring. Examples of dopants of this type are substituted or unsubstituted tristilbenamines or further dopants which are described, for example, in WO 06/000388 and the as yet unpublished patent applications DE 102004031000.9, EP 04028407.7 and EP 05001891.0. In addition, compounds in accordance with DE 102005023437.2 are preferred.

On use of the compounds of the formula (1) as host for phosphorescent dopants, one or more substituents $R^1$ preferably contain at least one group C=O, P(=O)($R^2$) and/or $SO_2$. These groups are particularly preferably bonded directly to the central unit according to the invention and furthermore particularly preferably contain one or, in the case of phosphine oxide, two further aromatic substituents. This applies, in particular, to the radicals $R^1$ on the structures of the formulae (2a), (3a) and (4a).

In phosphorescent devices, the dopant is preferably selected from the class of the metal complexes containing at least one element having an atomic number of greater than 20, preferably greater than 38 and less than 84, particularly preferably greater than 56 and less than 80. The phosphorescent emitters used are preferably metal complexes which contain molybdenum, tungsten, rhenium, ruthenium, osmium, rhodium, iridium, palladium, platinum, silver, gold or europium, in particular iridium or platinum. Phosphorescent materials as are used in accordance with the prior art are generally suitable for this purpose.

It is furthermore preferred for the compounds of the formula (1) to be employed as emitting materials if at least one substituent $R^1$ contains at least one vinylaryl unit, at least one stilbene unit and/or at least one arylamino unit. This applies, in particular, to the radicals $R^1$ on the structures of the formulae (2a), (3a) and (4a).

The proportion of the compound of the formula (1) in the mixture of the emitting layer is between 0.1 and 50.0% by weight, preferably between 0.5 and 20.0% by weight, particularly preferably between 1.0 and 10.0% by weight. The proportion of the host material is correspondingly between 50.0 and 99.9% by weight, preferably between 80.0 and 99.5% by weight, particularly preferably between 90.0 and 99.0% by weight.

Suitable host materials are then various classes of substance. Preferred host materials are selected from the classes of the oligoarylenes (for example 2,2',7,7'-tetraphenylspirobifluorene in accordance with EP 676461 or dinaphthylanthracene), in particular the oligoarylenes containing fused aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with the as yet unpublished application EP 04026402.0) or the boronic acid derivatives (for example in accordance with the as yet unpublished application EP 05009643.7). Suitable host materials are furthermore the above-described compounds according to the invention. Apart from the compounds according to the invention, particularly preferred host materials are selected from the classes of the oligoarylenes containing naphthalene, anthracene and/or pyrene or atropisomers of these compounds, the oligoarylene-vinylenes, the ketones, the phosphine oxides and the sulfoxides. In addition to the compounds according to the invention, very particularly preferred host materials are selected from the classes of the oligoarylenes containing anthracene and/or pyrene or atropisomers of these compounds, the phosphine oxides and the sulfoxides. For the purposes of this invention, an oligoarylene will be taken to mean a compound in which at least three aryl or arylene groups are bonded to one another.

In still a further embodiment of the invention, the compounds of the formula (1) are employed as hole-transport material or as hole-injection material. The compounds are then preferably substituted by at least one group $N(Ar)_2$, preferably by at least two groups $N(Ar)_2$. This applies, in particular, to the radicals $R^1$ on the structures of the formulae (2a), (3a) and (4a). The compound is preferably employed in a hole-transport layer or in a hole-injection layer. For the purposes of this invention, a hole-injection layer is a layer which is directly adjacent to the anode. For the purposes of this invention, a hole-transport layer is a layer which is located between a hole-injection layer and an emission layer. If the compounds of the formula (1) are used as hole-transport material or as hole-injection material, it may be preferred for them to be doped with electron-acceptor compounds, for example with $F_4$-TCNQ or with compounds as described in EP 1476881 or EP 1596445.

It is furthermore preferred for the compounds of the formula (1) to be employed as electron-transport material. It may be preferred here for one or more substituents $R^1$ to contain at least one group C=O, P(=O)($R^2$) and/or $SO_2$. These groups are particularly preferably bonded directly to the central unit according to the invention and furthermore particularly preferably also contain one or, in the case of phosphine oxide, two further aromatic substituents. It may furthermore be preferred for the compound to be doped with electron-donor compounds. This applies, in particular, to the radicals $R^1$ on the structures of the formulae (2a), (3a) and (4a). It may furthermore be preferred for the compound to be doped with electron-donor compounds.

Compounds of the formula (1) may also be employed in polymers either as polymer backbone, as emitting unit and/or as hole-transporting unit. The preferred substitution patterns here correspond to those described above.

Preference is furthermore given to an organic electroluminescent device, characterised in that one or more layers are coated by means of a sublimation method. In this, the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are coated by means of the OVPD (organic vapour phase deposition) process or with the aid of carrier-gas sublimation. The materials are applied here at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or inkjet printing. Soluble compounds of the formula (1) are necessary for this purpose. High solubility can be achieved through suitable substitution of the compounds The compounds according to the invention have high efficiency and high stability on use in organic electroluminescent devices, which is evident, in particular, from a long lifetime. In addition, the compounds have a high glass transition temperature.

The present application text is directed to the use of the compounds according to the invention in relation to OLEDs and PLEDs and the corresponding displays. In spite of this restriction of the description, it is possible for the person skilled in the art, without further inventive step, also to employ the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

The present invention likewise relates to the use of the compounds according to the invention in the corresponding devices and to these devices themselves.

The invention is explained in greater detail by the following examples, without wishing for them to be restricted thereby.

EXAMPLES

The following syntheses were carried out under a protective-gas atmosphere, unless indicated otherwise. The starting materials were purchased from ALDRICH or ABCR. 1,4-Naphthalenediboronic acid was synthesised as described in *Journal of Organic Chemistry* 2000, 65(13), 3952-3960.

Example 1

Synthesis of 4,10-tetramethyl-4H-10H-fluoreno[4,3,2-de]-anthracene and 5,8-tetramethyl-5,8-dihydrobenzo[rst]pentaphene a) 1,4-Bis(2-methoxycarbonylphenyl)naphthalene

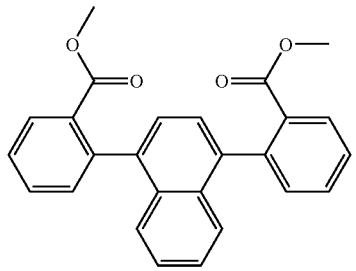 [SMILES: COC(=O)c1ccccc1-c1ccc(-c2ccccc2C(=O)OC)c2ccccc12]

1.55 g (0.1 mmol) of Pd(PPh$_3$)$_4$ are added to a vigorously stirred, degassed suspension of 21.6 g (7.1 mmol) of methyl 2-bromobenzoate, 10.1 g (28 mmol) of 1,4-naphthalenediboronic acid and 18.9 g (6.6 mmol) of trispotassium phosphate in a mixture of 350 ml of water and 350 ml of THF, and the mixture is refluxed for 60 h. After cooling, the organic phase is separated off, washed three times with 200 ml of water and once with 200 ml of saturated sodium chloride solution and subsequently dried over magnesium sulfate. The organic phase is evaporated to dryness under reduced pressure in a rotary evaporator. The grey residue obtained in this way is recrystallised from dioxane. The deposited crystals are filtered off with suction, washed with 50 ml of ethanol and subsequently dried under reduced pressure. Yield: 13 g, 82% of theory.

b) 1,4-Bis(2-methanol-α,α-dimethylphenyl)naphthalene

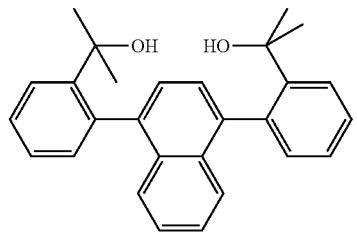 [SMILES: CC(C)(O)c1ccccc1-c1ccc(-c2ccccc2C(C)(C)O)c2ccccc12]

30 g (75 mmol) of 1,4-bis(2-methoxycarbonylphenyl)naphthalene are initially introduced in 2000 ml of THF under nitrogen, cooled to −78° C., and 175 ml (378 mmol) of 2.2M methyllithium solution are added dropwise. The mixture is subsequently stirred at −78° C. for 16 h. The mixture is allowed to come to room temperature overnight. After hydrolysis using 125 ml of saturated NH$_4$Cl solution, the precipitate is filtered off with suction and washed with ethyl acetate. The filtrate is extracted twice with water, and the organic phase is dried over Na$_2$SO$_4$. The residue after evaporation of the solvent is purified by chromatography (toluene/ethyl acetate 6:4). Yield: 27 g, 93% of theory.

c) 4,10-Tetramethyl-4H-10H-fluoreno[4,3,2-de]anthracene and 5,8-tetramethyl-5,8-dihydrobenzo[rst]pentaphene

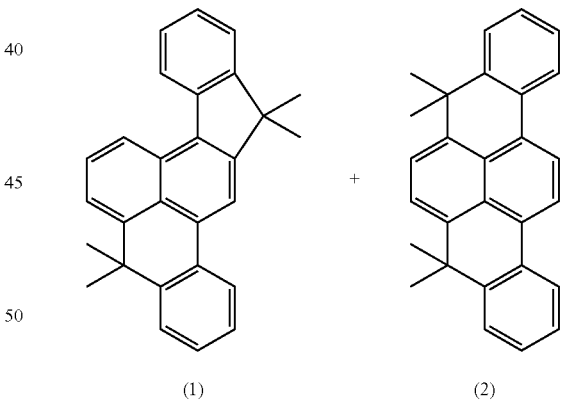

200 g of polyphosphoric acid are initially introduced. 25 g (63.05 mmol) of 1,4-bis(2-methanol-α,α,-dimethyl)phenyl)naphthalene are subsequently added. The mixture is stirred at room temperature for 20 h. Ice-water is then slowly added to the mixture. The precipitated solid is filtered off with suction, dried in a drying cabinet and recrystallised from ethyl acetate. Yield:

4,10-tetramethyl-4H-10H-fluoreno[4,3,2-de]anthracene (1): 9.9 g (45% of theory)

5,8-tetramethyl-5,8-dihydrobenzo[rst]pentaphene (2): 6.6 g (30% of theory)

Example 2

Synthesis of 5,8-tetra(p-tert-butylphenyl)-5,8-dihydrobenzo[rst]pentaphene and 4,10-tetra(p-tert-butylphenyl)-4H-10H-fluoreno[4,3,2-de]anthracene a) 1,4-Bis[2-methanol-α,α-di(p-tert-butylphenyl)phenyl]naphthalene

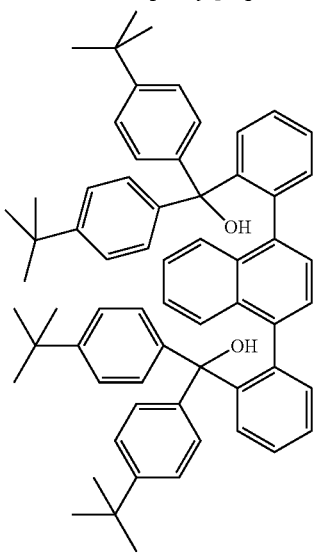

8.5 g (40 mmol) of 1-bromo-4-tert-butylbenzene are initially introduced in 50 ml of THF under nitrogen, cooled to −75° C., 25 ml (40 mmol) of 1.6M n-butyllithium solution are added dropwise, and the mixture is stirred at this temperature for 2 h. 3.56 g (9 mmol) of 1,4-bis(2-methoxycarbonyl-phenyl)naphthalene (synthesised as described in Example 1a), dissolved in 50 ml of THF, are subsequently added dropwise at such a rate that the temperature does not exceed −65° C. The mixture is allowed to come to room temperature overnight. After hydrolysis using 200 ml of water, the precipitate is filtered off with suction, rinsed with EtOH and recrystallised from ethyl acetate. Yield: 15.8 g, 85% of theory.

b) 5,8-Tetra(p-tert-butylphenyl)-5,8-dihydrobenzo[rst]pentaphene and 4,10-tetra(p-tert-butylphenyl)-4H-10H-fluoreno[4,3,2-de]anthracene

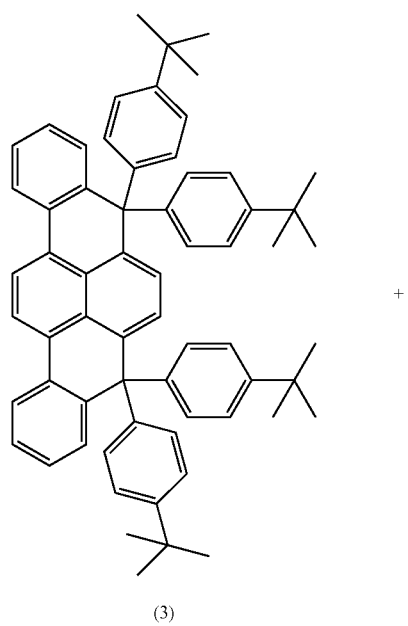

(3)

+

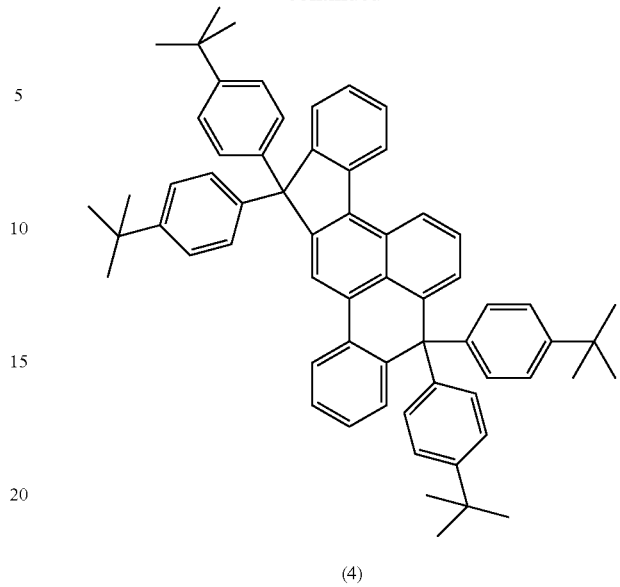

(4)

9.7 g (11.2 mmol) of 1,4-bis[2-methanol-α,α-di(p-tert-butylphenyl)phenyl]-naphthalene are initially introduced in 120 ml of glacial acetic acid, and the mixture is stirred for 10 min. 0.5 ml of HCl (conc.) is subsequently added, and the mixture is refluxed for 1 h. Ice-water is then slowly added to the mixture. The precipitated solid is filtered off with suction, dried in a drying cabinet and recrystallised from toluene.

Yield:

5,8-tetra(p-tert-butylphenyl)-5,8-dihydrobenzo[rst]pentaphene (3): 5.8 g, 50% of theory 4,10-tetra(p-tert-butylphenyl)-4H-10H-fluoreno[4, 3,2-de]anthracene (4): 2.8 g, 30% of theory

Example 3

Synthesis of amine D1 a) Bromination of compound (1)

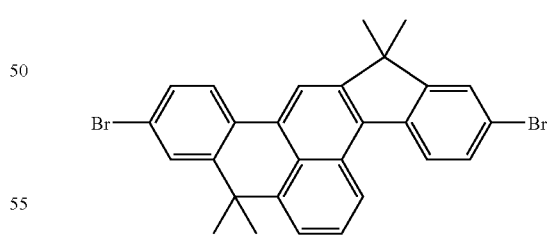

9.0 g (25 mmol) of 4,10-tetramethyl-4H-10H-fluoreno[4,3,2-de]anthracene (1) are initially introduced in 300 ml of dichloromethane with exclusion of light and cooled to 5° C. 2.7 ml (50 mmol) of bromine in 25 ml of dichloromethane are added dropwise over the course of 15 min., and the mixture is stirred at 5° C. for a further 7 h. When conversion is complete, the reaction is terminated by addition of 15 ml of ethanol, and the product is filtered off with suction, washed a number of times with ethanol and subsequently recrystallised twice from NMP, giving 11.2 g (86% of theory) of a pale-yellow solid which, according to HPLC, has a purity of >99.7%.

b) Synthesis of amine D1

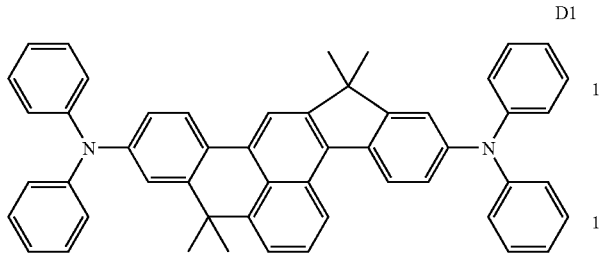

D1

11.2 g (22 mmol) of the bromine compound from Example 3a) and 9.7 g (58 mmol) of diphenylamine are suspended in 250 ml of anhydrous toluene. 190 mg (0.9 mmol) of tri-tert-butylphosphine and 107 mg (0.5 mmol) of Pd(OAc)$_2$ and 6.3 g (66 mmol) of NaO$^t$Bu are subsequently added, and the reaction mixture is refluxed for 4 h. When the reaction is complete, 150 ml of water are added, and the solid is filtered off with suction, washed with ethanol and dried. Recrystallisation five times from NMP, extraction twice with boiling ethanol and subsequent sublimation twice (330° C., 2×10$^{-5}$ mbar) gives 11.8 g (77%) of a pale-yellow solid having a purity of >99.9% according to HPLC.

Examples 4 to 6

Synthesis of the amines D2, D3 and D4

Analogously to Example 3, the corresponding bis(diphenylamine) derivatives are synthesised from compounds (2), (3) and (4) (synthesised as described in Examples 1 and 2) by bromination and Hartwig-Buchwald coupling. The structures of D2, D3 and D4 are depicted below;

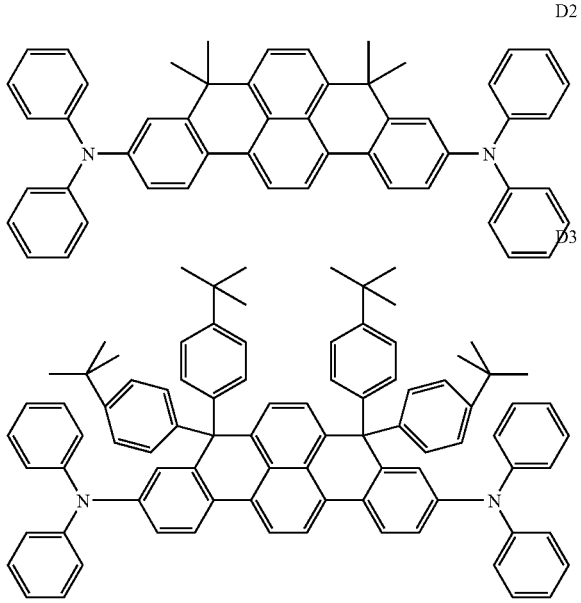

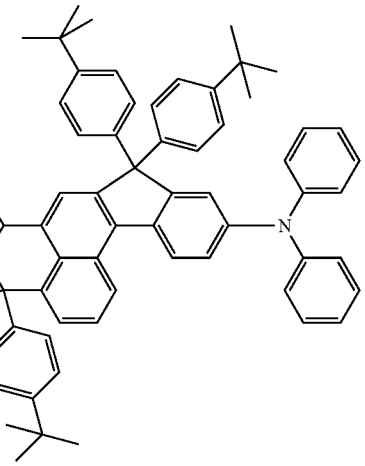

D4

Example 7

Production of OLEDs

OLEDs are produced by a general process as described in WO 04/058911, which is adapted in individual cases to the particular circumstances (for example layer-thickness variation in order to achieve optimum efficiency or colour).

The results for various OLEDs are presented in the following examples. The basic structure, the materials and layer thicknesses used, apart from the emitting layer and the hole-injection layer, are identical for better comparability. OLEDs having the following structure are produced analogously to the above-mentioned general process:

| | |
|---|---|
| Hole-injection layer (HIL) | 0 nm or 20 nm HIL1, see Table 1 |
| Hole-transport layer (HTL) | 40 nm or 20 nm NPB (vapour-deposited; N-naphthyl-N-phenyl-4,4'-diaminobiphenyl) |
| Emission layer (EML) | see Table 1 for materials, concentration and layer thickness |
| Electron conductor (ETL) | 20 nm AlQ$_3$ (purchased from SynTec; tris(quinolinato)aluminium(III)) |
| LiF/Al (cathode) | 1 nm LiF, 150 nm Al on top. |

These OLEDs are characterised by standard methods. For this purpose, the electroluminescence spectra, the efficiency (measured in cd/A), the power efficiency (measured in lm/W) as a function of the brightness, calculated from current/voltage/luminance characteristic lines (IUL characteristic lines), and the lifetime are determined. The lifetime is defined as the time after which the initial brightness of 1000 cd/m$^2$ has dropped to half.

Table 1 shows the results for some OLEDs (Examples 8 to 11), with the composition of the EML and HTL, including the layer thicknesses, also being shown in each case. The OLEDs here comprise the compounds according to the invention either as hole-injection material (use of D3 in Examples 9 and 11), as host material in the emitting layer (use of (3) in Examples 8 and 9) and/or as dopant in the emitting layer (use of D3 in Examples 10 and 11). The structures of the host material H1 and of the dopant D5 are shown below:

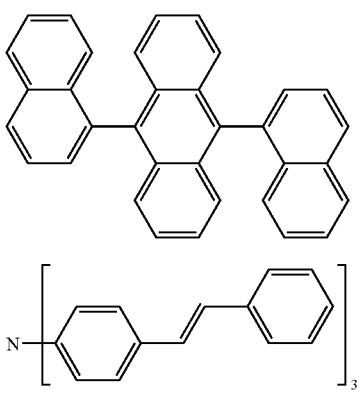

H1

D5

TABLE 1

| Ex. | HIL | HTL2 | EML | Max. eff. (cd/A) | U (V) at 1000 cd/m² | CIE$^a$ | Lifetime (h)$^b$ |
|---|---|---|---|---|---|---|---|
| 8 | — | NPB (40 nm) | (3):D5 (5%) (30 nm) | 3.8 | 6.8 | x = 0.15 y = 0.11 | 700 |
| 9 | D3 (20 nm) | NPB (20 nm) | (3):D5 (5%) (30 nm) | 4.0 | 6.0 | x = 0.15 y = 0.11 | 2200 |
| 10 | — | NPB (40 nm) | H1:D3 (5%) (30 nm) | 9.0 | 5.6 | x = 0.18 y = 0.24 | 5500 |
| 11 | D3 (20 nm) | NPB (20 nm) | H1:D3 (5%) (30 nm) | 11.0 | 5.8 | x = 0.18 y = 0.24 | 8000 |

$^a$CIE coordinates: colour coordinates of the Commission Internationale de l'Eclairage 1931.
$^b$Lifetime: time until the brightness drops to 50% of the initial brightness, measured at an initial brightness of 1000 cd/m².

In summary, it can be stated that OLEDs comprising compounds of the formula (1) have very long lifetimes and good efficiencies, as can easily be seen from Table 1. These compounds are therefore very highly suitable for use in OLEDs.

The invention claimed is:

1. An organic electronic device comprising at least one compound of formulae (2), (3), or (4)

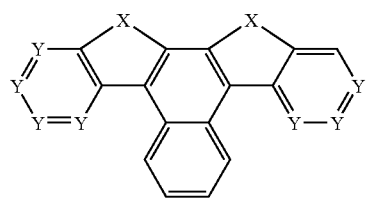

Formula (2)

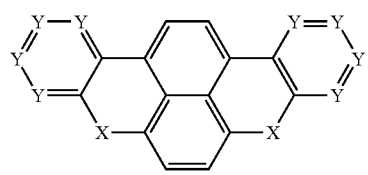

Formula (3)

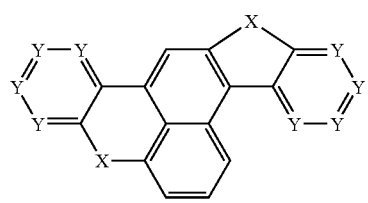

Formula (4)

wherein
the naphthalene group is optionally substituted by one or more radicals $R^1$ Y is on each occurrence, identically or differently, $CR^1$ or N;

$R^1$ is, identically or differently on each occurrence, H, F, Cl, Br, I, $N(Ar)_2$, $C(=O)Ar$, $P(=O)(Ar)_2$, $S(=O)Ar$, $S(=O)_2Ar$, $CR^2=CR^2Ar$, CN, $NO_2$, $Si(R^2)_3$, $B(OR^2)_2$, a straight-chain alkyl, alkoxy or thioalkoxy group having up to 40 C atoms, or a branched or cyclic alkyl, alkoxy or thioalkoxy group having 3 to 40 C atoms, in each case optionally substituted by one or more radicals $R^2$, wherein one or more non-adjacent $CH_2$ groups are optionally replaced by $-R^2C=CR^2-$, $-C\equiv C-$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $-NR^2-$, $-O-$, $-S-$, or $-CONR^2-$ and wherein one or more H atoms is optionally replaced by F, Cl, Br, I, CN, or $NO_2$, an aromatic or heteroaromatic ring system having 5 to 40 aromatic ring atoms optionally substituted by one or more radicals $R^2$, or an aryloxy or heteroaryloxy group having 5 to 40 aromatic ring atoms optionally substituted by one or more radicals $R^2$, or a combination of these systems; and wherein two or more adjacent substituents $R^1$ optionally define a mono- or polycyclic aliphatic ring system with one another, wherein two groups $R^1$ on one group $C(R^1)_2$ optionally define a spiro structure, and Ar is on each occurrence an aromatic or heteroaromatic ring system having 5-30 aromatic ring atoms optionally substituted by one or more non-aromatic radicals $R^1$; wherein two radicals Ar on the same nitrogen atom are optionally linked to one another by a single bond or a bridge X;

$R^2$ is, identically or differently on each occurrence, H or an aliphatic, aromatic, or heteroaromatic hydrocarbon radical having up to 20 C atoms; wherein two or more adjacent substituents $R^2$ optionally define a mono- or polycyclic aliphatic or aromatic ring system with one another;

X is, identically or differently on each occurrence, a divalent bridge selected from the group consisting of $C(R^1)_2$, $C=O$, $C=NR^1$, O, S, $S=O$, $SO_2$, $N(R^1)$, $P(R^1)$, $P(=O)$ $R^1$, $C(R^1)_2-C(R^1)_2$, $C(R^1)_2-C(R^1)_2-C(R^1)_2$, $C(R^1)_2-O$, and $C(R^1)_2-O-C(R^1)_2$; and wherein at least one substituent $R^1$ containing at least one aryl or heteroaryl group is present.

2. The organic electronic device of claim 1, wherein said device is selected from the group consisting of organic electroluminescent devices, organic field-effect transistors, organic thin-film transistors, organic light-emitting transistors, organic integrated circuits, organic solar cells, organic field-quench devices, light-emitting electrochemical cells, organic laser diodes, and organic photoreceptors.

3. The organic electronic device of claim 1, wherein said compound is selected from the structures of formulae (2a), (3a) or (4a)

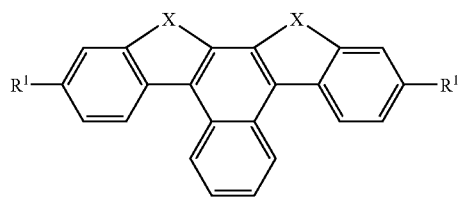

Formula (2a)

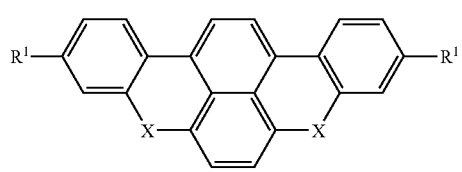

Formula (3a)

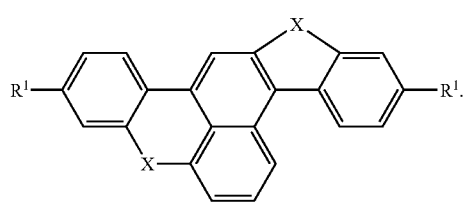

Formula (4a)

4. The organic electronic device of claim 1, wherein $R^1$ is, identically or differently on each occurrence, H, F, C(=O)Ar, P(=O)(Ar)$_2$, —CR$^2$=CR$^2$Ar, a straight-chain alkyl group having up to 5 C atoms or a branched alkyl group having 3 to 5 C atoms, wherein one or more non-adjacent CH$_2$ groups is optionally replaced by —R$^2$C=CR$^2$—, —C≡C—, or —O— and wherein one or more H atoms is optionally replaced by F, an aryl group having 6 to 16 C atoms, a heteroaryl group having 2 to 16 C atoms, or a spirobifluorene group, optionally substituted in each case with one or more radicals R$^2$, or a combination of two or three of these systems, or wherein $R^1$ is, identically or differently on each occurrence, a group of formula (5) or (6)

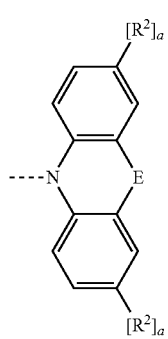

Formula (5)

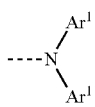

Formula (6)

wherein
E is a single bond, O, S, N(R$^2$), or C(R$^2$)$_2$;
Ar$^1$ is, identically or differently on each occurrence, an aryl or heteroaryl group having 5 to 20 aromatic ring atoms or a triarylamine group having 15 to 30 aromatic ring atoms, in each case optionally substituted by one or more radicals R$^2$;
a is, identically or differently on each occurrence, 0 or 1 wherein at least one substituent R$^1$ containing at least one aryl or heteroaryl group is present.

5. The organic electronic device of claim 4, wherein Ar$^1$ is, identically or differently on each occurrence, an aryl or heteroaryl group having 6 to 14 aromatic ring atoms or a triarylamine group having 18 to 22 aromatic ring atoms, in each case optionally substituted by one or more radicals R$^2$.

6. An organic electroluminescent device comprising an anode, a cathode, and at least one emitting layer, wherein said at least one emitting layer comprises a mixture of at least one compound of formulae (2), (3), or (4)

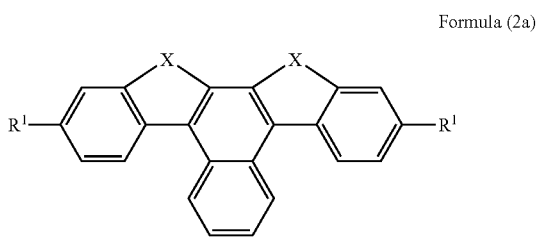

Formula (2a)

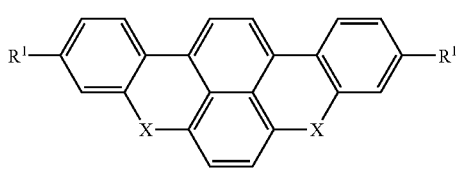

Formula (3a)

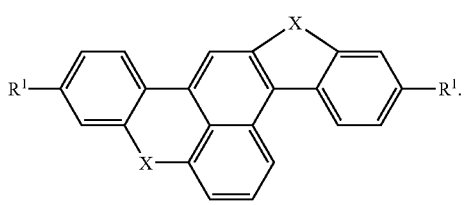

Formula (4a)

wherein
the naphthalene group is optionally substituted by one or more radicals R$^1$
Y is on each occurrence, identically or differently, CR$^1$ or N;
R$^1$ is, identically or differently on each occurrence, H, F, Cl, Br, I, N(Ar)$_2$, C(=O)Ar, P(=O)(Ar)$_2$, S(=O)Ar, S(=O)$_2$Ar, CR$^2$=CR$^2$Ar, CN, NO$_2$, Si(R$^2$)$_3$, B(OR$^2$)$_2$, a straight-chain alkyl, alkoxy or thioalkoxy group having up to 40 C atoms, or a branched or cyclic alkyl, alkoxy or thioalkoxy group having 3 to 40 C atoms, in each case optionally substituted by one or more radicals R$^2$, wherein one or more non-adjacent CH$_2$ groups are optionally replaced by —R²C=CR²—, —≡C—, Si(R²)₂, Ge(R²)₂, Sn(R²)₂, C=O, C=S, C=Se, C=NR², P(=O)(R²), SO, SO₂, —NR²—, —O—, —S—, or —CONR²— and wherein one or more H atoms is optionally replaced by F, Cl, Br, I, CN, or NO₂, an aromatic or heteroaromatic ring system having 5 to 40 aromatic ring atoms optionally substituted by one or more radicals R², or an aryloxy or heteroaryloxy group having 5 to 40 aromatic ring atoms optionally substituted by one or more radicals R², or a combination of these systems; and wherein two or more adjacent substituents R¹ optionally define a mono- or polycyclic aliphatic ring system with one another, wherein two groups R¹ and one group C(R¹)₂ optionally define a spiro structure, and Ar is on each occurrence an aromatic or heteroaromatic ring system having 5-30 aromatic ring atoms optionally substituted by one or more non-aromatic radicals R¹; wherein two radicals Ar on the same nitrogen atom are optionally linked to one another by a single bond or a bridge X;

R² is, identically or differently on each occurrence, H or an aliphatic, aromatic, or heteroaromatic hydrocarbon radical having up to 20 C atoms; wherein two or more adjacent substituents R² optionally define a mono- or polycyclic aliphatic or aromatic ring system with one another;

X is, identically or differently on each occurrence, a divalent bridge selected from the group consisting of C(R¹)₂, C=O, C=NR¹, O, S, S=O, SO₂, N(R¹), P(R¹), P(=O)R¹, C(R¹)₂—C(R¹)₂, C(R¹)₂—C(R¹)₂—C(R¹)₂, C(R¹)₂—O, and C(R¹)₂—O—C(R¹)₂; and wherein at least one substituent R¹ containing at least one aryl or heteroaryl group is present with at least one fluorescent or phosphorescent dopant and/or a mixture of said at least one compound with at least one host material.

7. The organic electronic device of claim 6, wherein said at least one compound is employed as hole-transport material in a hole-transport layer and/or a hole-injection layer and/or said at least one compound is employed as electron-transport material in an electron-transport layer.

8. The organic electroluminescent device of claim 6, wherein said compound is selected from the structures of formulae (2a), (3a) or (4a)

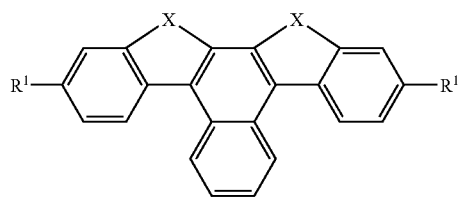

Formula (2a)

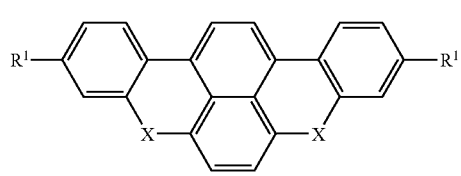

Formula (3a)

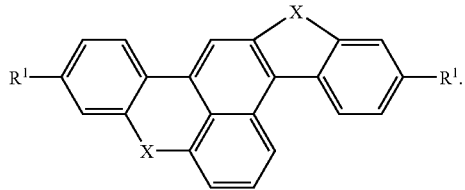

Formula (4a)

9. The organic electroluminescent device of claim 6, wherein R¹ is, identically or differently on each occurrence, H, F, C(=O)Ar, P(=O)(Ar)₂, —CR²=CR²Ar, a straight-chain alkyl group having up to 5 C atoms or a branched alkyl group having 3 to 5 C atoms, wherein one or more non-adjacent CH₂ groups is optionally replaced by —R²C=CR²—, —C≡C—, or —O— and wherein one or more H atoms is optionally replaced by F, an aryl group having 6 to 16 C atoms, a heteroaryl group having 2 to 16 C atoms, or a spirobifluorene group, optionally substituted in each case with one or more radicals R², or a combination of two or three of these systems, or wherein R¹ is, identically or differently on each occurrence, a group of formula (5) or (6)

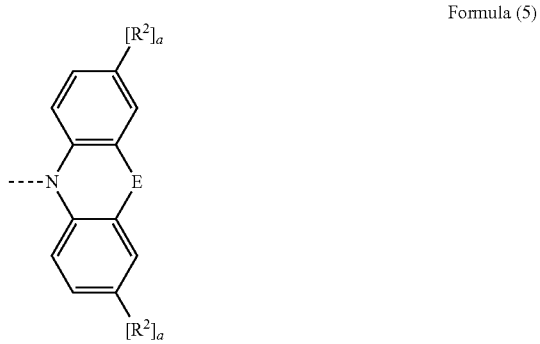

Formula (5)

Formula (6)

wherein

E is a single bond, O, S, N(R²), or C(R²)₂;

Ar¹ is, identically or differently on each occurrence, an aryl or heteroaryl group having 5 to 20 aromatic ring atoms or a triarylamine group having 15 to 30 aromatic ring atoms, in each case optionally substituted by one or more radicals R²;

a is, identically or differently on each occurrence, 0 or 1 wherein at least one substituent R¹ containing at least one aryl or heteroaryl group is present.

10. The organic electroluminescent device of claim 9, wherein Ar¹ is, identically or differently on each occurrence, an aryl or heteroaryl group having 6 to 14 aromatic ring atoms or a triarylamine group having 18 to 22 aromatic ring atoms, in each case optionally substituted by one or more radicals R².

11. A compound of formulae (2), (3), or (4)

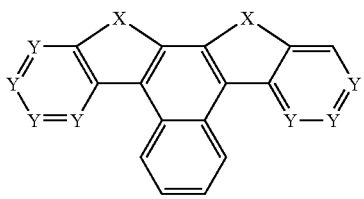

Formula (2)

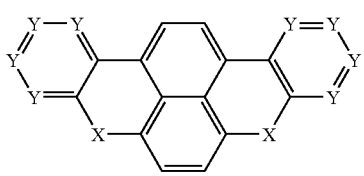

Formula (3)

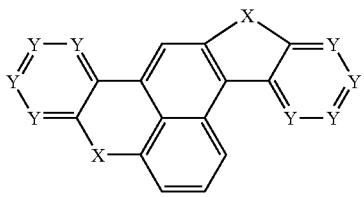

Formula (4)

wherein the naphthalene group is optionally substituted by one or more radicals $R^1$;

Y is on each occurrence, identically or differently, $CR^1$ or N;

$R^1$ when it is not part of a divalent bridge, is, identically or differently on each occurrence, H, F, C(=O)Ar, P(=O)(Ar)$_2$, —$CR^2$=$CR^2$Ar, a straight-chain alkyl group having up to 5 C atoms or a branched alkyl group having 3 to 5 C atoms, wherein one or more non-adjacent CH$_2$ groups is optionally replaced by —$R^2C$=$CR^2$—, —C≡C—, or —O— and wherein one or more H atoms is optionally replaced by F, an aryl group having 6 to 16 C atoms, a heteroaryl group having 2 to 16 C atoms, or a spirobifluorene group, optionally substituted in each case with one or more radicals $R^2$, or a combination of two or three of these systems, or wherein $R^1$ is, identically or differently on each occurrence, a group of formula (5) or (6)

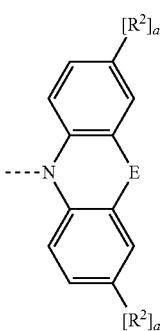

Formula (5)

Formula (6)

wherein

E is a single bond, O, S, N($R^2$), or C($R^2$)$_2$;

$Ar^1$ is, identically or differently on each occurrence, an aryl or heteroaryl group having 5 to 20 aromatic ring atoms or a triarylamine group having 15 to 30 aromatic ring atoms, in each case optionally substituted by one or more radicals $R^2$.

a is, identically or differently on each occurrence, 0 or 1;
with the proviso that when $R^1$ is part of a divalent bridge X, $R^1$ is, identically or differently on each occurrence, F, C(=O)Ar, P(=O)(Ar)$_2$, $CR^2$=$CR^2$Ar, a straight-chain alkyl group having 1 to 5 C atoms, a branched alkyl group having 3 to 5 C atoms, wherein one or more non-adjacent CH$_2$ groups are optionally replaced by —$R^2C$=$CR^2$—, —C≡C—, or —O—, and wherein one or more H atoms is optionally replaced by F, an aryl group having 6 to 16 C atoms, or a heteroaryl group having 2 to 16 C atoms, or a spirobifluorene group, wherein said straight-chain alkyl, branched alkyl, aryl, and heteroaryl groups are, in each case, optionally substituted by one or more radicals $R^2$, or a combination of two or three of these groups, or a group of formula (5) or (6)

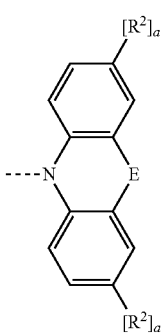

Formula (5)

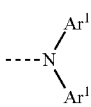

Formula (6)

wherein

E is a single bond, O, S, N($R^2$), or C($R^2$)$_2$;

Ar1 is, identically or differently on each occurrence, an aryl or heteroaryl group having 5 to 20 aromatic ring atoms or a triarylamine group having 15 to 30 aromatic ring atoms, which are in each case optionally substituted by one or more radicals $R^2$;

a is, identically or differently on each occurrence, 0 to 1;

Ar is on each occurrence an aromatic or heteroaromatic ring system having 5-30 aromatic ring atoms optionally substituted by one or more non-aromatic radicals $R^1$; wherein two radicals Ar on the same nitrogen atom are optionally linked to one another by a single bond or a bridge X;

$R^2$ is, identically or differently on each occurrence, H or an aliphatic, aromatic, or heteroaromatic hydrocarbon radical having up to 20 C atoms; wherein two or more adjacent substituents $R^2$ optionally define a mono- or polycyclic aliphatic or aromatic ring system with one another;

X is, identically or differently on each occurrence, a divalent bridge selected from $C(R^1)_2$, $C=O$, O, S, and $N(R^1)$; and wherein at least one substituent $R^1$ containing at least one aryl or heteroaryl group is present.

12. The compound of claim 11, wherein said compound is selected from the structures of formulae (2a), (3a) or (4a)

Formula (2a)

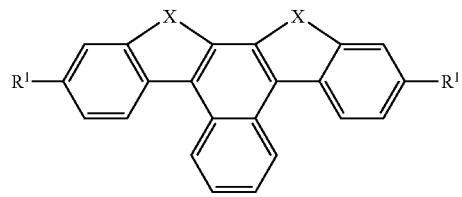

Formula (3a)

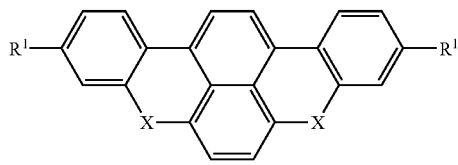

Formula (4a)

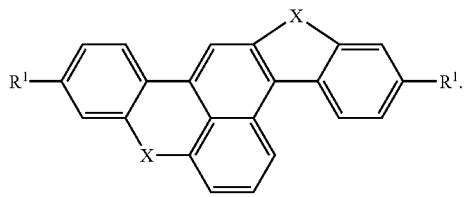

13. The compound of claim 11, wherein $Ar^1$ is, identically or differently on each occurrence, an aryl or heteroaryl group having 6 to 14 aromatic ring atoms or a triarylamine group having 18 to 22 aromatic ring atoms, in each case optionally substituted by one or more radicals $R^2$.

* * * * *